US006660725B1

(12) United States Patent
Reiner et al.

(10) Patent No.: US 6,660,725 B1
(45) Date of Patent: *Dec. 9, 2003

(54) METHOD AND COMPOSITION FOR MODULATING AMYLOIDOSIS

(75) Inventors: Peter B. Reiner, Vancouver (CA); Fred Chiu-lai Lam, Vancouver (CA)

(73) Assignee: The University of British Columbia, Vancouver (CA)

(*) Notice: Subject to any disclaimer, the term of this patent is extended or adjusted under 35 U.S.C. 154(b) by 64 days.

This patent is subject to a terminal disclaimer.

(21) Appl. No.: 09/643,511

(22) Filed: Aug. 22, 2000

(65) Prior Publication Data (65)

Related U.S. Application Data

(60) Division of application No. 09/177,413, filed on Oct. 23, 1998, now Pat. No. 6,514,688, and a continuation-in-part of application No. 09/067,523, filed on Apr. 28, 1998, now abandoned, which is a continuation-in-part of application No. 08/847,616, filed on Apr. 28, 1997, now abandoned.

(51) Int. Cl.$^7$ .......................... A61K 31/56; C07J 53/00
(52) U.S. Cl. .................. 514/169; 514/2; 514/9; 435/52; 552/502; 552/503; 540/2
(58) Field of Search .................. 514/2, 9, 169; 530/317, 322, 395; 552/502, 503; 540/2; 435/52

(56) References Cited

U.S. PATENT DOCUMENTS

| | | | | |
|---|---|---|---|---|
| 4,117,118 | A |   | 9/1978 | Harri et al. .................. 424/177 |
| 5,281,607 | A |   | 1/1994 | Stone et al. .................. 514/280 |
| 5,385,915 | A | * | 1/1995 | Buxbaum et al. ............ 514/313 |
| 5,635,496 | A |   | 6/1997 | Daynes et al. ............... 514/169 |
| 5,753,640 | A |   | 5/1998 | Araneo et al. ............... 514/178 |
| 5,780,484 | A |   | 7/1998 | Zelle et al. .................. 514/316 |
| 5,811,434 | A |   | 9/1998 | Zelle et al. .................. 514/307 |
| 5,840,736 | A |   | 11/1998 | Zelle et al. .................. 514/332 |
| 5,858,719 | A |   | 1/1999 | Hillman et al. ............. 435/69.1 |

FOREIGN PATENT DOCUMENTS

| | | |
|---|---|---|
| EP | 0363212 | 6/1989 |
| WO | WO 94/18972 | 9/1994 |
| WO | WO 98/20891 | 5/1998 |
| WO | WO 98/20892 | 5/1998 |
| WO | WO 98/20893 | 5/1998 |
| WO | WO 98/48784 | 11/1998 |
| WO | WO 99/10340 | 3/1999 |

OTHER PUBLICATIONS

Kell er al. "SDZ PSC 833, A Non–Immunosuppressive Cyclosporine: Its Potency In Overcoming P–Glycoprotein–Mediated Multidrug Resistance Of Murine Leukemia" Int. J. Cancer, vol. 50, pp. 593–597. 1992.*

Patel, "Pharmacotherapy Of Cognitive Impairment In Alzheimer's Disease: A Review", J. Geriatr. Psychiatry Neurol. vol. 8, pp. 81–95, 1995.*

Abe et al. 1991 "Selective induction of Kunitz–type protease inhibitor domain–containing amyloid precursor protein mRNA after persistent focal ischemia in rat cerebral cortex" Neurosci Lett 125:172–4.

Allikmets et al. 1996 "Characterization of the human ABC superfamily: isolation and mapping of 21 new genes using the Expressed Sequence Tags database" Hum. Mol. Gen., 5:1649–1655.

Baulieu 1989 "Contragestion and Other Clinical Applications of RU 486, an Antiprogesterone at the Receptor" Science, 245:1351–1357.

Becq et al. 1997 "ABC1, an ATP Binding Cassette Transporter Required for Phagocytosis of Apoptic Cells, Generates a Regulated Anion Flux after Expression in Xenopus laevis Oocytes" J. Biological Chemistry, 272:2695–2699.

Behl, et al., "Protection against oxidative stress–induced neuronal cell death; a novel role for RU–486," Eur. J. Neuroscience, 9(5):912–920 (1997).

Behl, et al., "Glucocorticoid enhance oxidative stress–induced cell death in hippocampal neurons in vitro," Endocrinology, 138(1):101–106 (1997).

Beller et al., "Efficacy of oral physostigmine in primary degenerative dementia", Psychopharmacology, 87:147–151 (1985).

Bierer, L.M. et al., "A pilot study of oral physostigmine plus yohimbine in patients with alzheimer disease," Alzheimer disease and associated disorders, 7(2):98–104 (Jan. 1993).

Birge, S.J. et al., "Is there a role for estrogen replacement therapy in the prevention and treatment of dementia?" Journal of the American Geriatrics Society, 44(7):865–870, 878–880 (1996).

(List continued on next page.)

Primary Examiner—Brenda Brumback
Assistant Examiner—Anish Gupta
(74) Attorney, Agent, or Firm—Seed IP Law Group PLLC

(57) ABSTRACT

Methods for modulating amyloid deposition in a subject are described. An effective amount of at least one ATP binding cassette (ABC) transporter blocker is administered to a subject, such that modulation of amyloid deposition occurs. Methods also include administering and effective amount of at least one ABC transporter blocker, or a pharmaceutically acceptable salt thereof, to a subject such that a disease state associated with amyloidosis is treated. Packaged pharmaceutical compositions for treating amyloidosis are described. The package includes a container for holding an effective amount of a pharmaceutical composition and instructions for using the pharmaceutical composition for treatment of amyloidosis. The pharmaceutical composition includes at least one ABC blocker for modulating amyloid deposition in a subject. Methods for identifying agents which modulate amyloid deposition in a subject are also described. An effective amount of at least one ATP binding cassette (ABC) transporter blocker is administered to an organism, such that modulation of amyloid deposition occurs.

3 Claims, 12 Drawing Sheets

OTHER PUBLICATIONS

Blank, C., "Anticortisols (Ru–486) can help many, says developer," *Drug Topics*, 141(23):30–32 (1997).

Borchelt et al. "Familial Alzheimer's Disease–Linked Presenilin 1 Variants Elevate AB1–42/1–40 Ratio In Vitro and In Vivo" *Neuron* vol. 17 (1996) 1005–1013.

Brann et al. "Emerging Diversities in the Mechanism of Action of Steroid Hormones" *J. Steroid Biochem. Molec. Biol.* vol. 52 (1995) 113–133.

Busciglio et al. "Generation of B–amyloid in the secretory pathway in neuronal and nonneuronal cells" *Proc. Natl. Acad. Sci. USA* vol. 90 (1993) 2092–2096.

Buxbaum et al. "Processing of Alzheimer B/A4 amyloid precursor protein: Modulation by agents that regulate protein phosphorylation" *Proc. Natl. Acad. Sci. USA* vol. 87 (1990) 6003–6006.

Buxbaum et al. "Protein phoshphorylation inhibits production of Alzheimer amyloid B/A4 peptide" *Proc. Natl. Acad. Sci. USA* vol. 90 (1993) 9195–9198.

Buxbaum et al. "Cholinergic agonists and interleukin 1 regulate processing and secretion of the Alzheimer B/A4 amyloid protein precursor" *Proc. Natl. Acad. Sci. USA* vol. 89 (1992) 10075–10078.

Buxbaum et al. "Calcium regulates processing of the Alzheimer amyloid protern precursor in a protein kinase C–independent manner" *Proc. Natl. Acad. Sci. USA* vol. 91 (1994) 4489–4493.

Cai et al. "Release of Excess Amyloid B Protein From a Mutant Amyloid B Protein Precursor" *Science* vol. 259 (1993) 514–516.

Caporaso "Protein phosphorylation regulates secretion of Alzheimer B/A4 amyloid precursor protein" *Proc. Natl. Acad. Sci. USA* vol. 89 (1992) 3055–3059.

Cech, A.C. et al., "Glucocorticoid receptor blockade reverses postinjury macrophage suppression," *Arch. Surg.*, 129(12):1227–1232 (1994).

Citron et al. "Generation of Amyloid B Protein from its Precursor is Sequence Specific" *Neuron* vol. 14 (1995) 661–670.

Citron et al. "Mutation of the B–amyloid precursor protein in familial Alzheimer's disease increases B–protein production" *Nature* vol. 360 (1992) 672–674.

Chen et al. "Internal Duplication and Homology with Bacterial Transport Proteins in the mdr1 (P–Glycoprotein) Gene from Multidrug–Resistant Human Cells" *Cell* vol. 47 (1986) 381–389.

Chen et al. "Cloning of the cDNA for a Human Homologue of the Drosophila White Gene and Mapping to Chromosome 21q22.3" *Am. J. Hum. Genet.* vol. 59 (1996) 66–75.

Connors et al. "The Cloning of a Human ABC Gene (ABC3) Mapping to Chromosome 16p13.3" *Genomics* vol. 39 (1997) 231–234.

Croop et al. "Isolation and characterization of a mammalian homolog of the *Drosophila white* gene" *Gene* vol. 185 (1997) 77–85.

Desdouits–Magnen et al. "Regulation of secretion of Alzheimer Amyloid Precursor Protein by the Mitogen–Activated Protein Kinase Cascade" *J. Neurochem.* vol. 70 (1998) 524–530.

Dhainaut et al. "New triazine derivatives as potent modulators of multidrug resistance" *J. Medicinal Chemistry* vol. 35 (1992) 2481–2496.

Duff et al. "Increased amyloid–B42(43) in brains of mice expressing mutant presenilin 1" *Nature* vol. 383 (1996) 710–713.

Dyrks et al. "Amyloid precursor protein secretion and BA4 amyloid generation are not mutually exclusive" *FEBS Lett.* vol. 349 (1994) 210–214.

Dyrks et al. "Generation of BA4 from the amyloid protein precursor and fragments thereof" *FEBS* vol. 335 (1993) 89–93.

Endicott et al. "The Biochemistry of P–Glycoprotein–Mediated Multidrug Resistance" *Ann. Rev. Biochem.* vol. 58 (1989) 137–71.

Esch et al. "Cleavage of Amyloid B Peptide During Constitutive Processing of its Precursor" *Science* vol. 248 (1990) 1122–1124.

Fukushima et al. "Activation of the Secretory Pathway Leads to a Decrease in the intracellular Amyloidogenic Fragments Generated From the Amyloid Protein Precursor" *Biochem. Biophys. Res. Comm.* vol. 194 (1993) 202–207.

Fukuyama et al. "Nerve Growth Factor–Induced Neuronal Differentiation is accompanied by Differential Induction and Localization of the Amyloid Precursor Protein (APP) in PC–12 Cells and Variant PC12S Cells" *Mol. Brain Res.* vol. 17 (1993) 17–22.

Gabuzda et al. "Inhibition of B–Amyloid Production by Activation of Protein Kinase C." *J. Neurochem.* vol. 61 (1993) 1511–1518.

Games et al. "Alzheimer–Type Neuropathology in transgenic mice overexpressing V717F B–Amyloid precursor Protein" *Nature* vol. 373 (1995) 523–527.

Goate et al. "Segregation of a missense mutation in the amyloid precursor protein gene with familial Alzheimer's disease" *Nature* vol. 349 (1991) 704–706.

Gong, Q. et al., "The receptor mechanism of the effect of massive dose of glucocorticoid in the treatment of traumatic brain edema in rats," *Zhongguo Bingli Shengli Zazhi*, 12(4):384–386 (1996).

Gordon et al. "Applications of Combinatorial Technologies to Drug Discovery. 2. Combinatorial Organic Synthesis, Library Screening Strategies, and Future Directions" *J. Med. Chem.* vol. 37 (1994) 1385–1401.

Gottesman et al. "Biochemistry of Multidrug Resistance Mediated by the Multidrug Transporter" *Annu. Rev. Biochem.* vol. 62 (1993) 385–427.

Gravina et al. "Mmyloid B Protein (AB) in Alzheimer's Disease Brain Biochemical and Immunochemical analysis with antibodies specific for forms ending at AB40 or AB42(43)" *J. Biol. Chem.* vol. 270 (1995) 7013–7016.

Haass et al. "Amyloid B–peptide is produced by cultured cells during normal metabolism" *Nature* vol. 359 (1992) 322–325.

Hamon et al. "Interleukin–1B Secretion is Impaired by Inhibitors of the Atp Binding Cassette Transporter, ABC1" *Blood* vol. 90 (1997) 2911–2915.

Haring et al. "NGF Promotes Amyloid Precursor Protein Secretion via Muscarinic Receptor Activation" *Biochem. Biophys. Res. Comm.* vol. 213 (1995) 15–23.

Higaki et al. "Inhibition of B–Amyloid formation identifies proteolytic precursors and subcellular site of catabolism" *Neuron* vol. 14 (1995) 651–659.

Higgins "ABC Transporters: From microorganisms to man" *Annu. Rev. Cell Biol.* vol. 8 (1992) 67–113.

Higgins "Volume–activated chloride currents associated with the multidrug resistance P–glycoprotein" *J. Physiol.* vol. 482 (1995) 31s–36s.

Higgins et al. "Is the multidrug transporter a flippase?" *TIBS* vol. 17 (1992) 18–21.

Housley et al. "Isolation and Characterization of a mouse L cell variant deficient in glucocorticoid receptors" *Biochem. Biophys. Res. Comm.* vol. 164 (1989) 480–487.

Hasio et al. "Correlative mimory deficits, AB elevation, and amyloid plaques in transgenic mice" *Science* vol. 274 (1996) 99–102.

Hung et al. "Activation of protein kinase C inhibits cellular production of the amyloid B–protein" *J. Biol. Chem.* vol. 268 (1994) 8376–8382.

Hyde et al. "Structural model of ATP–binding proteins associated with cystic fibrosis, multidrug resistance and bacterial transport" *Nature* vol. 346 (1990) 362–365.

Ishida, T. et al., "Enhancement of murine serum amyloid A3 mRNA expression by glucocorticoids and its regulation by cytokines," *Journal of Leukocyte Biology*, 56(6):797–806 (Dec. 1994).

Jacobsen et al. "The release of Alzheimer's disease B amyloid peptide is reduced by phorbol treatment" *J. Biol. Chem.* vol. 269 (1994) 8376–8382.

Jette et al. "Isoform 1 (MDR3) is the MOR form of P–glycoprotein expressed in mouse brain capillaries. Evidence for cross–reactivity of antibody C219 with unrelated protein," *Biochem. J.* 1995, 305:761–766.

Kang et al. "The precursor of Alzheimer's disease amyloid A4 protein resembles a cell–surface recepor" *Nature*, vol. 325 (1987) 880–884.

Keller et al. "SDZ PSC 833, A non–immunosuppressive cyclosporine: its potency in overcoming P–glycoprotein–mediated multidrug resistance of murine leukemia" *Int. J. Cancer* vol. 50 (1992) 593–597.

Koo et al. "Evidence that production and release of amyloid B–protein involves the endocytic pathway" *J. Biol. Chem.* vol. 269 (1994) 17386–17389.

Kool et al. "Analysis of Expression of cMOAT (MRP2), MRP3, MRP4, and MRP5, Homologues of the Multidrug Resistance–associated Protein Gene (MRP1), in Human Cancer Cell Lines" *Cancer Research* vol. 57 (1997) 3537–3547.

Kremer et al. "Signal transduction by nerve growth factor and fivrovlast frowth factor in PC12 cells requires a sequence or Src and Ras Actions" *J. Cell Biol.* vol. 115 (1991) 809–819.

Kuller, L, ":Hormone Replacement Therapy and It's Potential Relationship to Dementia," JAGS, 44: 878–880.

Querfurth et al. "Calcium Ionophore Increases Amyloid β Peptide Production by Cultured Cells" *Biochem.* vol. 33 (1994) 4550–4561.

Raymond et al. "Functional Complementation of yeast ste6 by a mammalian multidrug resistance mdr gene" *Science* vol. 256 (1992) 232–234.

Reaume et al. "Enhanced Amyloidogenic Processing of the β–Amyloid Precursor Protein in Gene–targeted Mice Bearing the Swedish Familial Alzheimer's Disease Mutations and a "Humanized" Aβ Sequence" *J. Biol. Chem.* vol. 271 (1996) 23380–23388.

Roberts et al. "BA4 amyloid protein deposition in brain after head trauma" *The Lancet* vol. 338 (1991) 1422–1423.

Rogaev et al. "Familial Alzheimer's disease in kindreds with missense mutations in a gene on chromosone 1 related to the Alzheimer's disease type 3 gene" *Nature* vol. 376 (1995) 775–778.

Roses "Perspective On the Metabolism of Apolipoprotein E and the Alzheimer Diseases," *Exp. Neurol.* vol. 132 (1995) 149–156.

Savary et al. "Isolation and chromosomal mapping of a novel ATP–binding cassette transporter conserved in mouse and human" *Genomics* vol. 41 (1997) 275–278.

Scheuner et al. "Secreted amyloid β–protein similar to that in the senile plaques of Alzheimer's disease is increased in vivo by the presenilin 1 and 2 APP mutations linked to familial Alzheimer's disease" *Nature Medicine* vol. 2 (1996) 864–870.

Schubert et al. "The Regulation of Amyloid β Protein Precursor Secretion and Its Modulatory Role in Cell Adhesion" *Neuron* vol. 3 (1989) 689–694.

Selkoe "Normal and abnormal biology of the β–amyloid precursor protein" *Annu. Rev. Neurosci.* vol. 17 (1994) 489–517.

Seubert et al. "Isolation and quantification of soluble Alzheimer β–peptide from biological fluids" *Nature* vol. 359 (1992) 325–327.

Shapiro et al. "Reconstitution of Drug Transport by Purified P–glycoprotein" *Journal of Biological Chemistry* vol. 270 (1995) 16167–16175.

Sharma et al. "Peptide Transport by the Multidrug Resistance Pump" *J. Biol. Chem.* vol. 267 (1992) 5731–5734.

Shen et al. "Human multidrug–resistant cell lines: Increased mdr1 expression can precede gene amplification" *Science* vol. 232 (1986) 643–645.

Sherrington et al. "Cloning of a gene bearing missense mutations in early–onset familial Alzheimer's disease" *Nature* vol. 375 (1995) 754–760.

Shinoda H. et al. "In Vivo Circumvention of Vincristine Resistance in Mice with P388 Leukemia Using a Novel Compound, AHC–52" *Cancer Research* vol. 49 (1989) 1722–1726.

Shoji et al. "Production of the Alzheimer Amyloid β Protein by Normal Proteolytic Processing," *Science* vol. 258 (1992) 126–129.

Siman et al. "Expression of B–Amyloid precursor protein in reactive astrocytes following neuronal damage" *Neuron* vol. 3 (1989) 275–285.

Lam et al., "RU–486 regulates betaAPP processing," *Soc. Neuroscience abstracts*, 22(1–3):190 (1996).

Lebeau et al. "Steroid antagonists and receptor–associated proteins" *Human Reproduction* 9(Suppl) vol. 2 (1994) 11–21.

Lee et al. "Amyloid precursor protein processing is stimulated by metabotropic glutamate receptors" *Proc. Natl. Acad. Sci. USA* vol. 92 (1995) 8083–8087.

Lee et al. "The disordered neuronal cytoskeleton in Alzheimer's disease" *Curr. Opin. Neurobiol.* vol. 2 (1992) 653–656.

Luciani et al. "Cloning of Two Novel ABC Transporters Mapping on Human Chromosome 9" *Genomics* vol. 21 (1994) 150–159.

Mann et al. "The pattern of acquisition of plaques and tangles in the brains of patients under 50 years of age with Down's syndrome" *J. Neurol. Sci.* vol. 89 (1989) 169–179.

Martins et al. "High levels of amyloid–β protein from S182 (Glu$^{246}$) familial Alzheimer's cells" *Neuro Report* vol. 7 (1995) 217–220.

Masliah et al. "Comparison of Neurodegenerative Pathology in Transgenic Mice Overexpressing V717F β–Amyloid Precursor Protein and Alzheimer's Disease" *J. Neurosci.* vol. 16 (1996) 5795–5811.

Meyer et al. "Agonistic and antagonistic activities of RU486 on the functions of the human progesterone receptor" *EMBO J.* vol. 9 (1990) 3923–3932.

Mills et al. "Phorbol Esters but Not the Cholinergic Agonists Oxotremorine–M and Carbachol Increase Release of the Amyloid Precursor Protein in Cultured Rat Cortical Neurons" *J. Neurochem.* vol. 67 (1996) 1511–1518.

Mills et al. "Regulation of amyloid precursor protein catabolism involves the mitogen–activated protein kinase signal transduction pathway" *J. Neurosci.* vol. 17 (1997) 9415–9422.

Moguilewsky et al. "RU384486: Potent antiglucocorticoid activity correlated with strong binding to the cytosolic glucocorticoid receptor followed by an impaired activation" *J. Steroid Biochem.* vol. 20 (1984) 271–276.

Mohs et al., "Oral physostigmine treatment of patients with Alzheimer's disease," *Am. J. Psychiatry*, 142:28–33 (1985).

Mullan et al. "A pathogenic mutation for probable Alzheimer's disease in the APP gene at the N–terminus of β–amyloid" *Nature Genetics* vol. 1 (1992) 345–347.

Nitsch et al. "Serotonin 5–HT2a and 5–HT2c Receptors Stimulate Amyloid Precursor Protein Ectodomain Secretion" *J. Biol. Chem.* vol. 271 (1996) 4188–4194.

Nitsch et al. "Release of Alzheimer Amyloid Precursor Derivatives Stimulated by Activation of Muscarinic Acetylcholine Receptors" *Science* vol. 258 (1992) 304–307.

Perez et al. "Enhanced Release of Amyloid β–Protein from Codon 670/671 "Swedish" Mutant β–Amyloid Precursor Protein Occurs in Both Secretory and Endocytic Pathways" *J. Biol. Chem.* vol. 27 (1996) 19100–9107.

Poirier "Apolipoprotein E in aminal models of CNS injury and in Alzheimer's disease" *Trends Neurosci.* vol. 17 (1994) 525–530.

Sisodia et al. "Evidence That β–Amyloid Protein in Alzheimer's Disease Is Not Derived by Normal Processing" *Science* vol. 248 (1990) 492–495.

Slack et al. "Regulation by phorbol esters of amyloid precursor protein release from Swiss 3T3 Fibroblasts Overexpressing Protein Kinase Cα" J. Biol. Chem. vol. 268 (1993) 21097–21101.

Smith et al. "The human MDR3 P–glycoprotein promotes translocation of phosphatidylcholine through the plasma membrane of fibroblasts from transgenic mice" FEBS Letters vol. 354 (1994) 263–266.

Sturchler–Pierrat "Two amyloid precursor protein transgenic mouse models with Alzheimer disease–like pathology" *Proc. Natl. Acad. Sci. USA* vol. 94 (1997) 13287–13292.

Sugawara "L'expression and function of P–glycoprotein (MDR1 gene product) in normal malignant tissue," 1990, *Acta Pathol. Jap.* 40:545–553.

Suzuki et al. "An Increased Percentage of Long Amyloid β Protein Secreted by Familial Amyloid β protein Precursor (βAPP$_{717}$) Mutants" *Science* vol. 264 (1994) 1336–1340.

Tanzi et al. "Amyloid β Protein Gene: cDNA, mRNA Distribution, and Genetic Linkage Near the Alzheimer Locus" *Science* vol. 235 (1987) 880–884.

Teller et al. "Presence of soluble amyloid β–peptide precedes amyloid plaque formation in Down's syndrome" *Nature Medicine* vol. 2 (1996) 93–95.

Tuor, U.A., "Glucocorticoid and the prevention of hypoxic–ischemic brain damage," *Neuroscience and behavioural reviews*, 21(2):175–179 (1997).

Wehling et al. "Nongenomic Actions of Steroid Hormones" *Trends Endocrinol. Metab.* vol. 5 (1994) 347–353.

Weidermann et al. "Identification, Biogenesis, and Localization of Precursors of Alzheimer's Disease A4 Amyloid Protein" *Cell* vol. 57 (1989) 115–126.

Wilde–Bode et al. "Intracellular Generation and Accumulation of Amyloid B–Peptide terminating at amino acid 42" *J. Biol. Chem.* vol. 272 (1997) 16085–16088.

Wolf et al. "Muscarinic Regulation of Alzheimer's Disease Amyloid Precursor Protein Secretion and Amyloid β–Protein Production in Human Neuronal NT2N Cells" *J. Biol. Chem.* vol. 270 (1995) 4916–4922.

Yankner "Mechanisms of Neuronal Degeneration in Alzheimer's Disease" *Neuron* vol. 16 (1996) 921–932.

Zamora et al. "Physical–Chemical Properties Shared by Compounds That Modulate Multidrug Resistance in Human Leukemic Cells" *Mol. Pharmacol.* vol. 33 (1988) 454–462.

* cited by examiner

APP$_s$ ~97 kDa →

Control PMA RU486 DEX PROG DES

*Fig. 7*

97 kDa →

C PMA RU486

*Fig. 9*

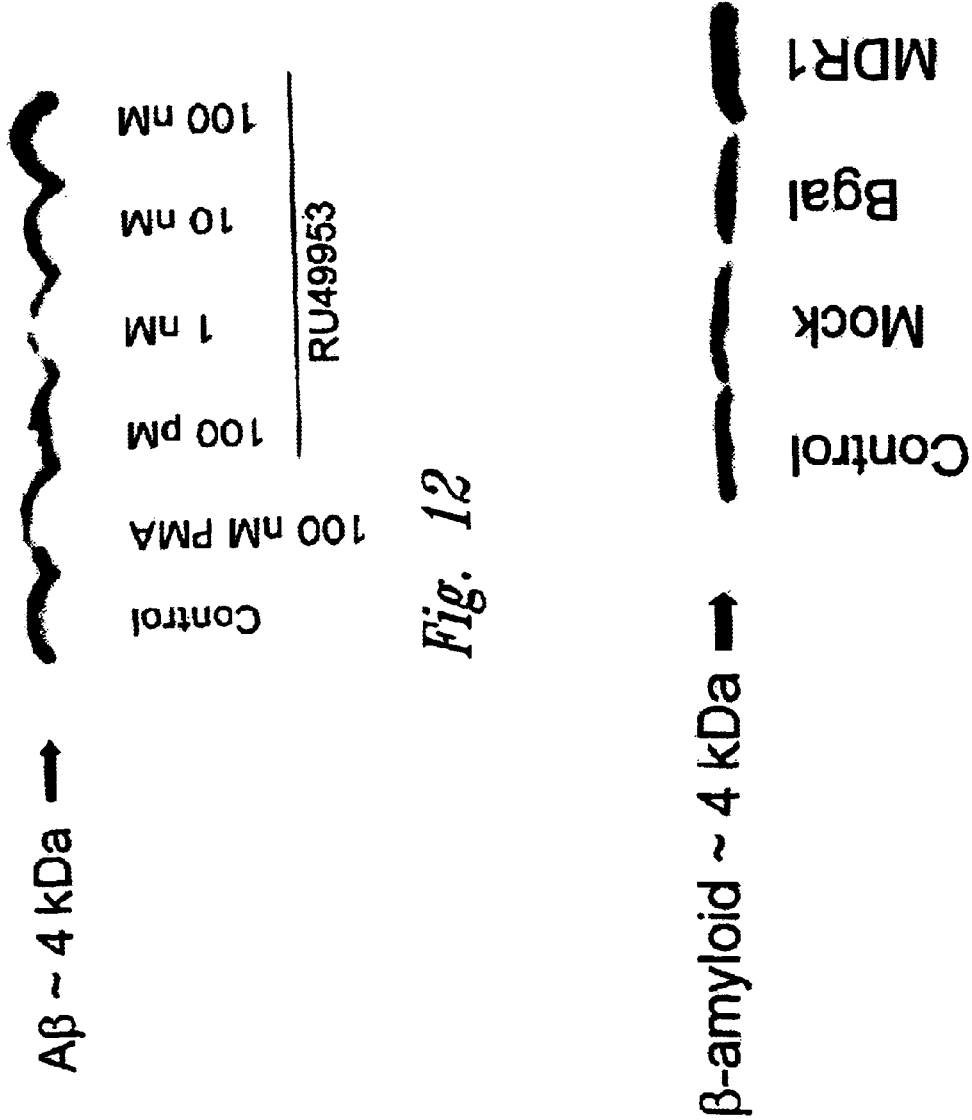

METHOD AND COMPOSITION FOR MODULATING AMYLOIDOSIS

RELATED APPLICATIONS

This application is a divisional application of Ser. No. 09/177,903, filed Oct. 23, 1998, now U.S. Pat. No. 8,874, 083 which in turn is a continuation-in-part of U.S. application Ser. No. 08/847,616, filed Apr. 28, 1997 now abandoned, and U.S. Pat. No. 09/067,523, filed Apr. 28, 1998now abandoned, the entire contents of which are incorporated herein by reference.

BACKGROUND OF THE INVENTION

Alzheimer's disease is a common dementing brain disorder of the elderly. The key features of the disease include progressive memory impairment, loss of language and visuospatial skills, and behavior deficits. These changes in cognitive function are the result of degeneration of neurons in the cerebral cortex, hippocampus, basal forebrain, and other regions of the brain. Neuropathological analyses of postmortem Alzheimer's diseased brains consistently reveal the presence of large numbers of neurofibrillary tangles in degenerated neurons and neuritic plaques in the extracellular space and in the walls of the cerebral microvasculature. The neurofibrillary tangles are composed of bundles of paired helical filaments containing hyperphosphorylated tau protein (Lee, V. M and Trojanowski, J. Q, The disordered Cytoskeleton in Alzheimer's disease, *Curr. Opin. Neurobiol.* 2:653 (1992)). The neuritic plaques consist of deposits of proteinaceous material surrounding an amyloid core (Selkoe, D. J., "Normal and abnormal biology of the β-amyloid precursor protein", *Annu. Rev. Neurosci.* 17:489–517 (1994)).

Evidence suggests that deposition of amyloid-β peptide (Aβ) plays a significant role in the etiology of Alzheimer's disease. A portion of this evidence is based upon studies which have been generated from data with regard to familial Alzheimer's disease. To date, this aggressive form of Alzheimer's disease has been shown to be caused by missense mutations in (at least) three genes: the amyloid precursor protein (APP) gene itself (Goate, A. et al., "Segregation of a missense mutation in the amyloid precursor protein gene with familial Alzheimer's disease", *Nature* 349:704–706 (1991) and Mullan, M. et al., "A pathogenic mutation for probable Alzheimer's disease in the APP gene at the N-terminus of β-amyloid", *Nature Genet.* 1:345–347 (1992)), and two genes termed presenilins 1 and 2 (Sherrington, R. et al., "Cloning of a gene bearing missense mutations in early-onset familial Alzheimer's disease", *Nature* 375:754–760 (1995) and Rogaev, E. I. et al., "Familial Alzheimer's disease in kindreds with missense mutations in a gene on chromosome 1 related to the Alzheimer's disease type 3 gene", *Nature* 376:775–778 (1995)). The missense mutations in APP are located in the region of the protein where proteolytic cleavage normally occurs (see below), and expression of at least some of these mutants results in increased production of Aβ (Citron, M. et al., "Mutation of the β-amyloid precursor protein in familial Alzheimer's disease increases β-amyloid production", *Nature* 360:672–674 (1992), Cai, X-D. et al., "Release of excess amyloid β protein from a mutant amyloid β protein precursor", *Science* 259:514–516 (1993) and Reaume, A. G. et al., "Enhanced amyloidogenic processing of the beta-amyloid precursor protein in gene-targeted mice bearing the Swedish familial Alzheimer's disease mutations and a humanized Aβ sequence", *J Biol. Chem.* 271:23380–23388 (1996)). Initial analyses of the structure of the presenilins did not suggest whether or not they might alter production of Aβ, however, recent data has indicated that these mutations cause an increase in Aβ secretion (Martins, R. N. et al., "High levels of amyloid-β protein from S182 (Glu$^{246}$) familial Alzheimer's cells", 7:217–220 (1995) and Scheuner, D. et al., "Secreted amyloid beta-protein similar to that in the senile plaques of Alzheimer's disease is increased in vivo by presenilin 1 and 2 and APP mutations linked to familial Alzheimer's disease", *Nature Medicine* 2:864–870 (1996); Borchelt DR, et al., "Familial Alzheimer's disease-linked presenilin 1 variants elevate Aβ1-42/1-40 ratio in vitro and in vivo," *Neuron* 17:1005–1013 (1996); Duff et al., "Increased amyloid-β42(43) in brains of mice expressing mutant presenilin 1," *Nature* 383:710–713 (1996); Scheuner et al., "Secreted amyloid β-protein similar to that in the senile plaques of Alzheimer's disease is increased in vivo by the presenilin 1 and 2 and APP mutations linked to familial Alzheimer's disease," *Nature* 2:864–870 (1996); Citron et al., "Mutant presenilins of Alzheimer's disease increase production of 42-residue amyloid β-protein in both transfected cells and transgenic mice," *Nature Medicine* 3:67–72 (1997). Tomita et al., "The presenilin 2 mutation (N141) linked to familial Alzheimer disease (Volga German families) increases the secretion of amyloid β protein ending at the 42$^{nd}$ (or 43$^{rd}$) residue" *Proc Natl Acad Sci USA* 94:2025–2030 (1997)). Thus, increased production of Aβ is associated with Alzheimer's disease. Corroborating evidence has been derived from at least two other sources. The first is that transgenic mice which express altered APP genes exhibit neuritic plaques and age-dependent memory deficits (Games, D. et al., "Alzheimer-type neuropathology in transgenic mice overexpressing V717F β-amyloid precursor protein", *Nature* 373:523–525 (1995); Masliah, E. et al., "Comparison of neurodegenerative pathology in transgenic mice overexpressing V717F β-amyloid precursor protein and Alzheimer's disease", *J Neurosci.* 16:5795–5811 (1996); Hsiao, K. et al., "Correlative memory deficits, Aβ elevation, and amyloid plaques in transgenic mice", *Science* 274:99–103 (1996); Sturchler-Pierrat et al., "Two amyloid precursor protein transgenic mouse models with Alzheimer disease-like pathology,"*Proc Natl Acad Sci USA* 94:13287–13292 (1997)). The second piece of evidence comes from study of patients suffering from Down's syndrome, who develop amyloid plaques and other symptoms of Alzheimer's disease at an early age (Mann, D. M. A. and M. M. Esiri, "The pattern of acquisition of plaques and tangles in the brains of patients under 50 years of age with Down's syndrome", *J Neurol. Sci.* 89:169–179 (1989)). Because the APP gene is found on chromosome 21, it has been hypothesized that the increased gene dosage which results from the extra copy of this chromosome accounts for the early appearance of amyloid plaques (Kang, J. et al., "The precursor protein of Alzheimer's disease amyloid A4 protein resembles a cell-surface receptor", *Nature* 325:733–736 (1987); Tanzi, R. E. et al., "Amyloid β protein gene: cDNA, mRNA distribution and genetic linkage near the Alzheimer locus", *Science* 235:880–884 (1987)). Taken together with the evidence derived from cases of familial Alzheimer's disease, the current data suggests that genetic alterations which result in an increase in Aβ production can induce Alzheimer's disease.

At present, less is understood about molecular modifications which are associated with the more common, sporadic form of Alzheimer's disease. It is well-established that allelic variation of apolipoprotein E is highly correlated with expression of Alzheimer's disease (Poirier, J., "Apolipoprotein E in animal models of CNS injury and in Alzheimer's disease", *Trends Neurosci.* 17:525–530 (1994); Roses, A. D. "Perspective on the metabolism of apolipoprotein E and the Alzheimer diseases",*Exp. Neurol.* 132:149–156 (1995)), but the mechanistic implications of this finding remain elusive. As in familial Alzheimer's disease (Suzuki, N. et al., "An increased percentage of long amyloid β protein secreted by familial amyloid β protein precursor (βAPP$_{717}$) mutants", *Science* 264:1336–1340 (1994)) and Down's syndrome (Teller, J. K. et al., "Presence of soluble amyloid β-peptide precedes amyloid plaque formation in Down's syndrome", *Nature Medicine* 2:93–95 (1996)), Aβ deposited in sporadic Alzheimer's disease plaques is typically a longer 42 amino acid version, Aβ$_{42}$ (Gravina, S. A. et al., "Amyloid beta protein (A beta) in Alzheimer's disease brain: Biochemical and immunocytochemical analysis with antibodies specific for forms ending at A beta 40 or A beta 42", *J Biol. Chem.* 270:7013–7016 (1995)). The suggestion that Aβ$_{42}$ is particularly pathogenic is consistent with data which demonstrate that this isoform is more lipophilic, aggregates more easily, and is more neurotoxic than its 40 amino acid cousin Aβ$_{40}$ (Yankner, B. A., "Mechanisms of neuronal degeneration in Alzheimer's disease", *Neuron* 16:921–932 (1996)). The Aβ$_{42}$ phenotypic similarity gives support to the hypothesis that sporadic Alzheimer's disease is also due to increased production of Aβ. What remains unclear is what the nature of the change is in sporadic Alzheimer's diseased brains which lead to increased production of Aβ. However, because Aβ deposition is an early and invariant event in Alzheimer's disease, it is believed that treatment which reduces production of Aβ will be useful in the treatment of this disease.

In addition to Alzheimer's disease, amyloidosis is also implicated in the pathophysiology of both stroke and head trauma. It is well established that neuronal trauma initiated either by cerebral ischemia such as that seen in stroke and head trauma all increase expression of APP and production of Aβ (Siman et al., "Expression of β-amyloid precursor protein in reactive astrocytes following neuronal damage." *Neuron* 3:275–285 (1989).; Abe et al., "Selective induction of kunitz-type protease inhibitor domain-containing amyloid precursor protein mRNA after persistent focal ischemia in rat cerebral cortex." *Neurosci Lett* 125:172–174 (1991).; Roberts et al., "β-A4 amyloid protein deposition in brain after head trauma." *Lancet* 338:1422–1423 (1991).; Gentleman et al., "β-Amyloid precursor protein (βAPP) as a marker for axonal injury after head injury." *Neurosci Lett* 160:139–144 (1993); Yokota et al., "Cytotoxic fragment of amyloid precursor protein accumulates in hippocampus after global forebrain ischemia," *J Cereb Blood Flow Metab* 16:1219–1223 (1996)). Indeed, the syndrome of dementia pugilistica which had been distinguished from Alzheimer's disease because of the absence of congophilic plaques (Corsellis et al., "The aftermath of boxing." *Psychological Med* 3:270–303 (1973)) has been shown to be characterized by large numbers of Aβ containing diffuse plaques (Roberts et al., "The occult aftermath of boxing, *J Neurol Neurosurg Psychiatry* 53:373–378(1990)). Moreover, cerebral amyloid angiopathy is a common feature of the brains of stroke patients with symptoms of dementia, focal neurological syndromes, or other signs of brain damage (Corio and Rubio, "Cerebral amyloid angiopathies", *Neuropath Appl Neurobiol* 22:216–227 (1996)). Taken together, these data suggest that production and deposition of Aβ may contribute to the pathology of Alzheimer's disease, head injury, and stroke.

A large body of data has accumulated regarding the production and deposition of both APP and Aβ. APP is an ubiquitous transmembrane glycoprotein (Selkoe, D. J., "Normal and abnormal biology of the β-amyloid precursor protein", *Annu. Rev. Neurosci.* 17:489–517 (1994)). Three major isoforms of APP are produced by alternative splicing: 751 and 770 amino acid isoforms contain a Kunitz protease inhibitor domain and are expressed both in neuronal and non-neuronal cells, while a 695 amino acid isoform lacks this domain and is expressed at high levels in neurons. Mature APP is turned over rapidly, with a half life of ~20–30 minutes. Embedded within the protein is a sequence of 39–43 amino acids which corresponds to the Aβ peptide.

Proteolytic processing of APP yields peptide fragments of varying size. An extensively studied degradative pathway is one in which the APP molecule is cleaved within the Aβ sequence (between residues 16 and 17) by a yet-to-be identified enzyme termed α-secretase. The resultant ~110–125 kDa soluble extracellular derivative termed APP$_S$ is rapidly released into the extracellular medium of cultured cells (Weidemann, A. et al., "Identification, biogenesis, and localization of precursors of Alzheimer's disease A4 amyloid protein", *Cell* 57:115–126 (1989); Esch, F. S. et al., "Cleavage of amyloid β peptide during constitutive processing of its precursor", *Science* 248:1122–1124 (1990); Sisodia S. S. et al., "Evidence that β-amyloid protein in Alzheimer's disease is not derived by normal processing", *Science* 248:492–495 (1990)); it is estimated that ~20% of the APP found on the membrane surface is released within 10 minutes (Koo, E. H. and S. L. Squazzo, "Evidence that production and release of amyloid β-protein involves the endocytic pathway",*J Biol. Chem.* 109:991–998 (1996)). Of particular significance is the fact that this constitutively active α-secretory pathway precludes the formation of intact Aβ and, presumably, amyloid deposition.

The Aβ peptide is secreted by cells (Haass, C. et al., "Amyloid β-peptide is produced by cultured cells during normal metabolism", *Nature* 359:322–325 (1992); Seubert, P. et al., "Isolation and quantitation of soluble Alzheimer β-peptide from biological fluids", *Nature* 359:325–357 (1992); Shoji, M. et al., "Production of the Alzheimer amyloid β protein by normal and proteolytic processing", *Science* 258:126–129 (1992); Busciglio, J. et al., "Generation of β-amyloid in the secretory pathway in neuronal and nonneuronal cells", *Proc. Natl. Acad Sci. USA* 90:2092–2096 (1993)). It is believed that secreted Aβ contributes to the deposition of insoluble amyloid in neuritic plaques (Selkoe, D. J., "Normal and abnormal biology of the β-amyloid precursor protein", *Annu. Rev. Neurosci.* 17:489–517 (1994)). Alternatively, Aβ may accumulate intracellularly and thereby initiate the disease process (Wild-Bode et al., "Intracellular generation and accumulation of amyloid β-peptide terminating at amino acid 42." *J. Biol. Chem.* 272:16085–16088 (1997)). As a result, considerable-effort is underway to unravel the molecular pathways mediating Aβ secretion. It appears that Aβ can be generated both via a classical secretory pathway (Dyrks, T. et al., "Amyloid precursor protein secretion and βA4 amyloid generation are not mutually exclusive", *FEBS Lett.* 349:210–214 (1994); Busciglio, J. et al., "Generation of β-amyloid in the secretory pathway in neuronal and nonneuronal cells",*Proc. Natl. Acad. Sci. USA* 90:2092–2096 (1993); Citron, M. et al., "Generation of amyloid β protein from its precursor is sequence specific",*Neuron* 14:662–670 (1995); Perez, R. G. et al., "Enhanced release of amyloid β-protein from codon 670/671 "Swedish" mutant β-amyloid precursor protein occurs in both secretory and endocytic pathways", *J Biol. Chem.* 271:9100–9107 (1996)), and after endocytosis of APP (Koo, E. H. and S. L. Squazzo, "Evidence that production and release of amyloid β-protein involves the endocytic pathway", *J Biol. Chem.* 109:991–998 (1996); Higaki, J. et al., "Inhibition of β-amyloid formation identifies proteolytic precursors and subcellular site of catabolism", *Neuron* 14:651–659 (1995); Perez, R. G. et al., "Enhanced release of amyloid β-protein from codon 670/671 "Swedish" mutant β-amyloid precursor protein occurs in both secretory and endocytic pathways", *J Biol. Chem.* 271:9100–9107 (1996)); however, many unknown details remain. Among these details is the mechanism by which Aβ exits the cell.

Although secretion of both $APP_S$ and Aβ is constitutive, the rate at which these two molecules are released from cells can be modified by activation of first and second messenger systems. $APP_S$ secretion is increased (Buxbaum, J. D. et al., "Processing of Alzheimer β/A4 amyloid precursor protein: Modulation by agents that regulate protein phosphorylation", *Proc. Natl. Acad. Sci. USA* 87:6003–6006 (1990); Caporaso, G. L. et al., "Protein phosphorylation regulates secretion of Alzheimer β/A4 amyloid precursor protein", *Proc. Natl. Acad. Sci. USA* 89:3055–3059 (1992); Slack, B. E. et al., "Regulation by phorbol esters of amyloid precursor protein release from Swiss 3T3 fibroblasts overexpressing protein kinase Cα", *J Biol. Chem.* 268:21097–21101 (1993); Mills, J. and P. B. Reiner, "Phorbol esters but not the cholinergic agonists oxotremorine-M and carbachol increase release of the amyloid precursor protein in cultured rat cortical neurons", *J Neurochem.* 67:1511–1518 (1996)) and Aβ secretion is decreased (Buxbaum, J. D. et al., "Protein phosphorylation inhibits production of Alzheimer amyloid β/A4 peptide", *Proc. Natl. Acad. Sci. USA* 90:9195–9198 (1993); Gabuzda, D. et al., "Inhibition of β-amyloid production by activation of protein kinase C", *J Neurochem.* 61:2326–2329 (1993); Hung, A. Y. et al., "Activation of protein kinase C inhibits cellular production of the amyloid β-protein", *J Biol. Chem.* 268:22959–22962 (1993); Jacobsen, J. S. et al., "The release of Alzheimer's disease β amyloid peptide is reduced by phorbol treatment", *J Biol. Chem.* 269:8376–8382 (1994)) by phorbol esters, presumably via activation of protein kinase C. Similar effects are seen following activation of membrane receptors thought to couple to protein kinase C (Buxbaum, J. D. et al., "Cholinergic agonists and interleukin 1 regulate processing and secretion of the Alzheimer β/A4 amyloid protein precursor", *Proc. Natl. Acad. Sci. USA* 89:10075–10078 (1992); Nitsch, R. M. et al., "5-HT2a and 5-HT2c receptors stimulate amyloid precursor protein ectodomain secretion", *J Biol. Chem.* 271:4188–4194 (1996); Nitsch, R. M. et al., "Release of Alzheimer amyloid precursor derivatives stimulated by activation of muscarinic acetylcholine receptors", *Science* 258:304–307 (1992); Lee, V. M. et al., "Amyloid precursor protein processing is stimulated by metabotropic glutamate receptors", *Proc. Natl. Acad. Sci. USA* 92:8083–8087 (1995); Wolf, B. A. et al., "Muscarinic regulation of Alzheimer's disease amyloid precursor protein secretion and amyloid β-protein production in human neuronal NT2N cells", *J Biol. Chem.* 270:4916–4922 (1995), MAP kinase (Mills et al., "Regulation of amyloid precursor protein catabolism involves the mitogen-activated protein kinase signal transduction pathway," *J Neurosci* 17:9415–9422 (1997); Desdouits-Magnen et al., "Regulation of secretion of Alzheimer amyloid precursor protein by the mitogen-activated protein kinase cascade," *J Neurochem* 70:524–530 (1998)), as does activation of nerve growth factor receptors (Schubert, D. et al., "The regulation of amyloid β protein precursor secretion and its modulatory role in cell adhesion", *Neuron* 3:689–694 (1989); Fukuyama, R. et al., "Nerve growth factor-induced neuronal differentiation is accompanied by differential induction and localization of the amyloid precursor protein (APP) in PC12 cells and variant PC12S cells", *Mol. Brain Res.* 17:17–22 (1993); Haring, R. et al., "NGF promotes amyloid precursor protein secretion via muscarinic receptor activation", *Biochem. Biophys. Res. Comm.* 213:15–23 (1995)) and increasing intracellular calcium (Buxbaum, J. D. et al., "Calcium regulates processing of the Alzheimer amyloid protein precursor in a protein kinase C-independent manner", *Proc. Natl. Acad. Sci. USA* 91:4489–4493 (1994); Querfurth, H. W. and D. J. Selkoe, "Calcium ionophore increases amyloid beta peptide production by cultured cells", *Biochem.* 33:4550–4561 (1994)).

In summary, Alzheimer's disease, stroke, e.g., cerebral ischemia, and head injury are characterized by cognitive and neurological deficits associated with extracellular and cerebrovascular amyloid deposits.

SUMMARY OF THE INVENTION

This invention provides methods, compositions, and screening methods which are useful in the treatment of amyloidosis. The methods of the invention involve administering to a subject a pharmaceutical composition including one or more agents which modulate (e.g., inhibit, prevent, or enhance) production and/or release of Aβ and ultimately, amyloid deposition. Accordingly, the methods and compositions of the invention are useful for inhibiting amyloidosis in disorders in which amyloid deposition occurs, e.g., Alzheimer's Disease, stroke and/or head trauma. The methods of the invention can be used therapeutically to treat amyloidosis or can be used prophylactically in a subject susceptible to amyloidosis. The methods of the invention are based, at least in part, on modulating cleavage of amyloid precursor protein (APP), the proteolytic processing of APP and/or exportation of amyloid-β protein (Aβ) by a blocker of a member of the ATP binding cassette (ABC) superfamily of transporters expressed in the brain or the cerebral microvasculature, e.g., MDR1, MDR3, ABC1, ABC2, ABC3, ABC7, ABC8, MRP4, MRP5 or the human ABC transporters encoded by the ESTs 45597, 122234, 123147, 131042, 157481, 182763, 352188 or 422562. Therefore, a therapeutic agent, such as a blocker, used in the method of the invention can modulate amyloid deposition.

The present invention provides methods for modulating amyloid deposition in a subject, by administering to the subject an effective amount of an ATP binding cassette (ABC) transporter or flippase blocker. In one preferred embodiment, the modulation includes preventing or inhibiting the amyloid deposition. The methods provide that one or more ABC transporter blockers or flippase blockers act to antagonize transport of Aβ through one or more ABC transporters or flippase blockers expressed in the brain or the cerebral microvasulature.

The present invention also provides methods for treating a disease state associated with amyloid deposition by administering to a subject an effective amount of at least one ABC transporter or flippase blocker, or a pharmaceutically acceptable salt thereof, such that a disease state associated with amyloidosis is treated. In one preferred embodiment, the amyloid deposition is associated with Alzheimer's Disease.

The present invention also provides methods for treating Alzheimer's disease by administering to a subject having Alzheimer's disease an effective amount of at least one ABC transporter or flippase blocker, or a pharmaceutically acceptable salt thereof, such that treatment occurs.

The present invention pertains to methods for treating head trauma by administering to a subject having head trauma an effective amount of at least one ABC transporter or flippase blocker, or a pharmaceutically acceptable salt thereof, such that treatment occurs.

The present invention also pertains to methods for treating stroke by administering to a subject affected by a stroke an effective amount of at least one ABC transporter or flippase blocker, or a pharmaceutically acceptable salt thereof, such that treatment occurs.

The present invention further pertains to packaged pharmaceutical compositions for treating amyloidosis. A packaged pharmaceutical composition includes a container which holds an effective amount of a pharmaceutical composition for modulating amyloid deposition in a subject. The pharmaceutical composition includes at least one ABC transporter or flippase blocker and instructions for using the pharmaceutical composition. In one preferred embodiment, the packaged pharmaceutical composition is for treatment associated with Alzheimer's Disease.

The present invention also pertains to methods for identifying agents which modulate amyloid deposition in an organism by administering to an organism an effective amount of at least one ATP binding cassette (ABC) transporter or flippase blocker, such that modulation of amyloid deposition occurs. The methods provide that one or more ABC transporter blockers or flippase blockers which act to antagonize transport of $A\beta$ through one or more ABC transporters or flippase blockers expressed in the brain or the cerebral microvasulature can be identified.

The present invention further pertains to methods for identifying agents which modulate transport or flipping of amyloid across a membrane, e.g., a cellular or synthetic membrane. The methods include introducing an agent into a model system containing the membrane, e.g., cellular or planar lipid membrane, ABC transporter and amyloid. The ability of the agent to modulate the transport or flipping of amyloid across the membrane is measured. The methods provide the ability to identify of one or more ABC transporter blockers or flippase blockers which act to antagonize transport of $A\beta$ through one or more ABC transporters or ABC transporters having flippase activity which are expressed in the brain or the cerebral microvasulature.

BRIEF DESCRIPTION OF THE DRAWINGS

FIG. 5 is a western blot of an SDS-PAGE gel demonstrating that RU-486 increases release of $APP_S$ from PC12 cells after an exposure of only 15 minutes.

FIG. 6 is a western blot of an SDS-PAGE gel demonstrating that RU-486 increases release of $APP_S$ from E-82 cells which lack progesterone and glucocorticoid receptors.

FIG. 7 is a western blot of a SDS-PAGE gel demonstrating that RU-486, Progesterone and Desmethoxyverapamil increase $APP_S$ secretion in PC12 cells.

FIG. 9 is a western blot of an SDS-PAGE gel demonstrating that RU-486 does not increase release of $APP_S$ from KB-3.1 cells which have minimal expression of p-glycoprotein.

FIG. 12 is a western blot of an SDS-PAGE gel demonstrating that RU-49953 decreases the release of $A\beta$ from SW cells.

FIG. 13 demonstrates transient transfection of P-glycoprotein increases basal secretion of $\beta$-amyloid.

DETAILED DESCRIPTION OF THE INVENTION

Figure 1:
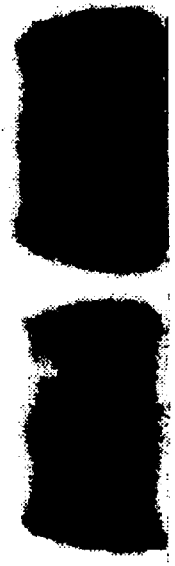
FIG. 1 is a western blot of an SDS-PAGE gel demonstrating that RU-486 increases release of $APP_S$ from PC12 cells.

The features and other details of the invention will now be more particularly described and pointed out in the claims. It will be understood that the particular embodiments of the invention are shown by illustration and not as limitations of the invention. The principal features of the invention can be employed in various embodiments without departing from the scope of the present invention. All parts and percentages are by weight unless otherwise stated.

The present invention pertains to methods for modulating amyloid deposition in a subject by administering to the subject an effective amount of at least one transport or flippase blocker for an ATP binding cassette (ABC) transporter which is expressed in the brain or cerebral microvasculature, such that modulation of amyloid deposition occurs. Amyloid deposition is a common problem associated with Alzheimer's disease, stroke and/or head trauma and is typically characterized by neuritic plaques. The present invention also pertains to methods for treating a disease state associated with amyloidosis by administering to a subject an effective amount of at least one ABC transporter blocker, or a pharmaceutically acceptable salt thereof, such that a disease state associated with amyloidosis is treated. The methods provide that one or more ABC transporter blockers or flippase blockers act to antagonize transport of $A\beta$ through one or more ABC transporters or flippase blockers expressed in the brain or the cerebral microvasulature.

The term ATP binding cassette (ABC) transporter is art recognized and includes the superfamily of transporters which use ATP as an energy source to transport various molecules against concentration gradients across cell membranes. Currently, there are at least 33 members of the ABC superfamily of transporters in humans. Of these, at least 12 have been identified following complete or partial sequencing of the gene, with an additional 21 members of the superfamily identified as expressed-sequence tags (ESTs) (Allikmets et al., "Characterization of the human ABC superfamily: isolation and mapping of 21 new genes using the Expressed Sequence Tags database", *Human Mol Genet-* ics 5:1649–1655 (1996)). Well-known examples of human ABC transporters include MDR1 and the cystic fibrosis transmembrane regulator, although examples of ABC transporters are also well-known in other species such as the chloroquine transporter of Plasmodium falciparum and the yeast transporter ste-6. Of the 33 putative human ABC transporters, evidence suggests that at least 16 may be expressed in the brain or its microvasculature. Examples of human ABC transporters which are expressed in the brain and its microvasculature include MDR1, MDR3, ABC1, ABC2, ABC3, ABC7, ABC8, MRP4, MRP5, and the human ABC transporters encoded by the ESTs 45597, 122234, 123147, 131042, 157481, 182763, 352188 and 422562.

The term "ABC transporter" is further intended to include a superfamily of genes found in many organisms including humans (Higgins CF, "ABC transporters:

from microorganisms to man", Annu Rev Cell Biol 8:67–113 (1992)) characterized by a highly conserved region known as the ATP binding cassette (Hyde et al., "Structural model of ATP-binding proteins associated with cystic fibrosis, multidrug resistance and bacterial transport", Nature 346:362–365 (1990); Mimura et al., "Structural model of the nucleotide binding conserved component of periplasmic permeases", Proc Natl Acad Sci USA 88:84–88 (1991)). These characteristic features provide a means of identifying unknown members of the ABC transporter superfamily using various database searching techniques, e.g. BLAST (Altschul et al., "Basic local alignment search tool," J Mol Biol 215:403–410 (1990)). Using the N-terminal ATP-binding domain of MDR1 as a conserved region of the superfamily of ABC transporters, this strategy has been utilized to identify a large family of ESTs corresponding to putative ABC transporters (Allikmets et al., "Characterization of the human ABC superfamily: isolation and mapping of 21 new genes using the Expressed Sequence Tags database", Human Mol Genetics 5:1649–1655 (1996)). The EST database can further be utilized as a first-pass means of examining expression of putative ABC transporters insofar as the expression library from which the EST derives can be used to provide partial information regarding the expression of the full-length gene. For example, an EST which is derived from an infant brain library is likely to be expressed in the brain.

The term "p-glycoprotein" is art recognized and is intended to include a subset of the family of ABC transporters. P-glycoproteins are large, glycosylated membrane proteins that can function as ATP-dependent efflux pumps, and are encoded by two genes in humans known as MDR1 and MDR3 and three genes in the mouse known as mdr1, mdr2, and mdr3 (Endicott, JA and Ling, V, "The biochemistry of p-glycoprotein-mediated multidrug resistance", Ann Rev Biochem 58:137–171 (1989)).

The term "MDR1" is art recognized and is intended to include the human MDR1 encoded gene product (GenBank Accession No. M14758; Chen et al., "Internal duplication and homology with bacterial transport proteins in the mdr1 (p-glycoprotein) gene from multidrug resistant human cells," Cell 47:381–389 (1986)) as well as its various isoforms as well as analogs, homologues, and orthologs in other species. The MDR1 gene product is an integral membrane protein having a predicted molecular weight of approximately 170 kDa, and has been shown to act as an ATP-dependent efflux pump with wide substrate specificity (Endicott, JA and Ling, V, "The biochemistry of p-glycoprotein-mediated multidrug resistance", Ann Rev Biochem 58:137–171 (1989)). The human MDR1 gene is expressed in the cerebral microvasculature and astrocytic foot processes (Thiebaut et al., "Immunohistochemical localization in normal tissues of different epitopes in the multidrug transport protein p170: evidence for localization in brain capillaries and crossreactivity of one antibody with a muscle protein." J Histochem Cytochem 37:159–164 (1989); Pardridge et al., "Brain microvascular and astrocyte localization of p-glycoprotein," J Neurochem 68:1278–1285 (1997)).

The term "MDR3" is art recognized and is intended to include the human MDR3 encoded gene product (GenBank Accession No. M23234; Chen et al., "Internal duplication and homology with bacterial transport proteins in the mdr1 (p-glycoprotein) gene from multidrug resistant human cells," Cell 47:381–389 (1986)) as well as its various isoforms as well as analogs, homologues, and orthologs in other species. The MDR3 gene product is an integral membrane protein and has been shown to promote translocation of phosphatidylcholine (Smith et al., "The human MDR3 p-glycoprotein promotes translocation of phosphatidylcholine through the plasma membrane of fibroblasts from transgenic mice" FEBS Lett 354:263–266 (1994)). A BLAST (Altschul et al., "Basic local alignment search tool," J Mol Biol 215:403–410 (1990)) search of GenBank predicts that human MDR3 is encoded by ESTs corresponding to gb-AA677416, gb-AA456377, gb-AA459824, gb-W22853, and gb-R53330 (best 5 matches listed only). Because at least one of these ESTs derives from an infant brain library, MDR3 is predicted to be expressed in brain. The term "ABC1" is art recognized and is intended to include the human ABC1 gene product and its various isoforms as well as analogs, homologues, and orthologs in other species. The mouse homologue of ABC1 has been cloned (EMBL Accession No. X75927, Luciani et al., "Cloning of two novel ABC transporters mapping on human chromosome 9," Genomics 21:150–159 (1994)) and may be involved in regulation of anion flux (Becq et al., "ABC1, an ATP binding cassette transporter required for phagocytosis of apoptotic cells, generates a regulated anion flux after expression in Xenopus laevis oocytes,", J Biol Chem 272:2695–2699 (1997)), and secretion of interleukin 1β (Hamon et al., "Interleukin-1b secretion is impaired by inhibitors of the ATP binding cassette transporter, ABC1," Blood 90:2911–2915 (1997)). The human gene encoding ABC1 has been partially cloned, is found on chromosome 9, and is expressed in brain (Luciani et al., "Cloning of two novel ABC transporters mapping on human chromosome 9," Genomics 21:150–159 (1994)). A BLAST (Altschul et al., "Basic local alignment search tool," J Mol Biol 215:403–410 (1990)) search of GenBank predicts that human ABC1 is encoded by ESTs corresponding to gb-U1 8236, gb-N46182, gb-H45142, gb-U66691, and gb-H21585 (best 5 matches listed only).

The term "ABC2" is art recognized and is intended to include the human ABC2 gene product and its various isoforms as well as analogs, homologues, and orthologs in other species. The mouse homologue of ABC2 has been cloned (EMBL Accession No.X75927, Luciani et al., "Cloning of two novel ABC transporters mapping on human chromosome 9," Genomics 21:150–159 (1994)). The human gene encoding ABC2 has been partially cloned, is found on chromosome 9, and is expressed in brain (Luciani et al., "Cloning of two novel ABC transporters mapping on human chromosome 9," Genomics 21:150–159 (1994)). A BLAST (Altschul et al., "Basic local alignment search tool," J Mol Biol 215:403–410 (1990)) search of GenBank predicts that human ABC2 is encoded by ESTs corresponding to gb-H39045, gb-U18235, gb-T33919, gb-W69928, and gb-M78056 (best 5 matches listed only).

The term "ABC3" is art recognized and is intended to include the human ABC3 gene product and its various isoforms as well as analogs, homologues, and orthologs in other species. The cDNA for human ABC3 (GenBank Accession No. U78735, Connors et al., "The cloning of a human ABC gene (ABC3) mapping to chromosome 16p13.3," *Genomics* 39:231–234 (1997)) is 5112 nucleotides in length, encoding 1704 amino acids with a predicted molecular weight of 191 kDa, is found on chromosome 16p13.3, and is expressed in brain.

The term "ABC7" is art recognized and is intended to include the human ABC7 gene product and its various isoforms as well as analogs, homologues, and orthologs in other species. The mouse homologue of ABC7 (abc7) has been partially cloned and is expressed in the brain (GenBank Accession No. U43892, Savary et al. "Isolation and chromosomal mapping of a novel ATP-binding cassette transporter conserved in mouse and human," *Genomics* 41:275–278 (1997)). A BLAST (Altschul et al., "Basic local alignment search tool," *J Mol Biol* 215:403–410 (1990)) search of GenBank predicts that human ABC7 is encoded by ESTs corresponding to gb-U66679, gb-AA403130, gb-AA626765, gb-AA668992, gb-AA733151 (best 5 matches listed only).

The term "ABC8" is art recognized and is intended to include the human ABC8 gene product and its various isoforms as well as analogs, homologues, and orthologs in other species. The gene encoding human ABC8 has been cloned (GenBank Accession No. U34919, Croop et al., "Isolation and characterization of a mammalian homologue of the Drosophila white gene," *Gene* 185:77–85 (1997); GenBank Accession No. X91249, Chen et al., "Cloning of the cDNA for a human homologue of the Drosophila white gene and mapping to chromosome 21q22.3," *Am J Human Genetics*. 59:66–75 (1996), and predicts a protein of (at least) 638 amino acids in length, homologous to the Drosophila white gene, mapping to chromosome 21q22.3, and is expressed in brain. Because there is no stop codon prior to the putative initiation methionine, it is unclear as to whether this represents the complete or partial sequence of human ABC8. The mouse homologue of human ABC8 (abc8) has been cloned and is also expressed in the brain (EMBL Accession No.Z48745, Savary et al. "Molecular cloning of a mammalian ABC transporter homologous to Drosophila white gene," *Mammalian Genome* 7:673–676 (1996); gb-u34920, Croop et al., "Isolation and characterization of a mammalian homologue of the Drosophila white gene," *Gene* 185:77–85 (1997)). A BLAST (Altschul et al., "Basic local alignment search tool," *J Mol Biol* 215:403–410 (1990)) search of GenBank predicts that human ABC8 is encoded by ESTs corresponding to gb-AA297078, gb-AA297109, gb-AA305082, gb-AA297995, and gb-AA297906 (best 5 matches listed only).

The term "MRP4" is art recognized and is intended to include the human MRP4 gene product and its various isoforms as well as analogs, homologues, and orthologs in other species. The human gene encoding MRP4 has been partially cloned, is found on chromosome 13 (GenBank Accession No U83660, Kool et al., "Analysis of expression of cMOAT (MRP2), MRP3, MRP4 and MRP5, homologues of the multidrug resistance-associate protein gene (MRP1), in human cancer cell lines," *Cancer Res* 57:3537–3547 (1997)). A BLAST (Altschul et al., "Basic local alignment search tool," *J Mol Biol* 215:403–410 (1990)) search of GenBank predicts that human MRP4 is encoded by ESTs gb-R35797, gb-U66686, gb-R35798, gb-N66654, and gb-AA015868 (best 5 matches listed only). Because at least one of these ESTs derives from an infant brain library, MRP4 is predicted to be expressed in brain.

The term "MRP5" is art recognized and is intended to include the human MRP5 gene product and its various isoforms as well as analogs, homologues, and orthologs in other species. The human gene encoding MRP5 has been partially cloned, is found on chromosome 3, and is expressed in brain (GenBank Accession No. U83661, Kool et al., "Analysis of expression of cMOAT (MRP2), MRP3, MRP4 and MRP5, homologues of the multidrug resistance-associate protein gene (MRP1), in human cancer cell lines," *Cancer Res* 57:3537–3547 (1997)). A BLAST (Altschul et al., "Basic local alignment search tool," *J Mol Biol* 215:403–410 (1990)) search of GenBank predicts that human MRP5 is encoded by ESTs gb-U66687, gb-H 17207, gb-AA829904, gb-H60893, gb-R34891 (best 5 matches listed only).

The term "human ABC transporter encoded by EST 45597" is art recognized and is intended to include the human EST 45597 gene product and its various isoforms as well as analogs, homologues, and orthologs in other species. EST 45597 was identified via BLAST (Altschul et al., "Basic local alignment search tool," *J Mol Biol* 215:403–410 (1990)) search of the public EST database using the N-terminal ATP-binding domain of MDR1 as a conserved region of superfamily of ABC transporters (Allikmets et al., "Characterization of the human ABC superfamily: isolation and mapping of 21 new genes using the Expressed Sequence Tags database", *Human Mol Genetics* 5:1649–1655 (1996)). Because EST 45597 is found in an infant brain library, the human ABC transporter encoded by EST 45597 is predicted to be expressed in the brain.

The term "human ABC transporter encoded by EST 122234" is art recognized and is intended to include the human EST 122234 gene product and its various isoforms as well as analogs, homologues, and orthologs in other species. EST 122234 was identified via BLAST (Altschul et al., "Basic local alignment search tool," *J Mol Biol* 215:403–410 (1990)) search of the public EST database using the N-terminal ATP-binding domain of MDR1 as a conserved region of superfamily of ABC transporters (Allikmets et al., "Characterization of the human ABC superfamily: isolation and mapping of 21 new genes using the Expressed Sequence Tags database", *Human Mol Genetics* 5:1649–1655 (1996)). Because EST 122234 is found in an infant brain library, the human ABC transporter encoded by EST 122234 is predicted to be expressed in the brain.

The term "human ABC transporter encoded by EST 123147" is art recognized and is intended to include the human EST 123147 gene product and its various isoforms as well as analogs, homologues, and orthologs in other species. EST 123147 was identified via BLAST (Altschul et al., "Basic local alignment search tool," *J Mol Biol* 215:403–410 (1990)) search of the public EST database using the N-terminal ATP-binding domain of MDR1 as a conserved region of superfamily of ABC transporters (Allikmets et al., "Characterization of the human ABC superfamily:

isolation and mapping of 21 new genes using the Expressed Sequence Tags database", *Human Mol Genetics* 5:1649–1655 (1996)). Because EST 123147 is found in an infant brain library, the human ABC transporter encoded by EST 123147 is predicted to be expressed in the brain.

The term "human-ABC transporter encoded by EST 131042" is art recognized and is intended to include the human EST 131042 gene product and its various isoforms as well as analogs, homologues, and orthologs in other species. EST 131042 was identified via BLAST (Altschul et al., "Basic local alignment search tool," *J Mol Biol* 215:403–410 (1990)) search of the public EST database using the N-terminal ATP-binding domain of MDR1 as a conserved region of superfamily of ABC transporters (Allikmets et al., "Characterization of the human ABC superfamily: isolation and mapping of 21 new genes using the Expressed Sequence Tags database", *Human Mol Genetics* 5:1649–1655 (1996)). Because EST 131042 is found in an infant brain library, the human ABC transporter encoded by EST 131042 is predicted to be expressed in the brain.

The term "human ABC transporter encoded by EST 157481 " is art recognized and is intended to include the human EST 45597 gene product and its various isoforms as well as analogs, homologues, and orthologs in other species. EST 157481 was identified via BLAST (Altschul et al., "Basic local alignment search tool," *J Mol Biol* 215:403–410 (1990)) search of the public EST database using the N-terminal ATP-binding domain of MDR1 as a conserved region of superfamily of ABC transporters (Allikmets et al., "Characterization of the human ABC superfamily: isolation and mapping of 21 new genes using the Expressed Sequence Tags database", *Human Mol Genetics* 5:1649–1655 (1996)). Because EST 157481 is found in an infant brain library, the human ABC transporter encoded by EST 157481 is predicted to be expressed in the brain.

The term "human ABC transporter encoded by EST 182763" is art recognized and is intended to include the human EST 182763 gene product and its various isoforms as well as analogs, homologues, and orthologs in other species. EST 182763 was identified via BLAST (Altschul et al., "Basic local alignment search tool," *J Mol Biol* 215:403–410 (1990)) search of the public EST database using the N-terminal ATP-binding domain of MDR1 as a conserved region of superfamily of ABC transporters (Allikmets et al., "Characterization of the human ABC superfamily: isolation and mapping of 21 new genes using the Expressed Sequence Tags database", *Human Mol Genetics* 5:1649–1655 (1996)). Because EST 182763 is found in an infant brain library, the human ABC transporter encoded by EST 182763 is predicted to be expressed in the brain.

The term "human ABC transporter encoded by EST 352188" is art recognized and is intended to include the human EST 352188 gene product and its various isoforms as well as analogs, homologues, and orthologs in other species. EST 352188 was identified via BLAST (Altschul et al., "Basic local alignment search tool," *J Mol Biol* 215:403–410 (1990)) search of the public EST database using the N-terminal ATP-binding domain of MDR 1 as a conserved region of superfamily of ABC transporters (Allikmets et al., "Characterization of the human ABC superfamily: isolation and mapping of 21 new genes using the Expressed Sequence Tags database", *Human Mol Genetics* 5:1649–1655 (1996)). Because EST 352188 is found in an infant brain library, the human ABC transporter encoded by EST 352188 is predicted to be expressed in the brain.

The term "human ABC transporter encoded by EST 422562" is art recognized and is intended to include the human EST 422562 gene product and its various isoforms as well as analogs, homologues, and orthologs in other species. EST 422562 was identified via BLAST (Altschul et al., "Basic local alignment search tool," *J Mol Biol* 215:403–410 (1990)) search of the public EST database using the N-terminal ATP-binding domain of MDR1 as a conserved region of superfamily of ABC transporters (Allikmets et al., "Characterization of the human ABC superfamily: isolation and mapping of 21 new genes using the Expressed Sequence Tags database", *Human Mol Genetics* 5:1649–1655 (1996)). Because EST 422562 is reported to be a housekeeping gene (Allikmets et al., "Characterization of the human ABC superfamily: isolation and mapping of 21 new genes using the Expressed Sequence Tags database", *Human Mol Genetics* 5:1649–1655 (1996)), the human ABC transporter encoded by EST 422562 is predicted to be expressed in the brain.

The term "transporter blocker" is intended to include those compounds that can modulate ABC transporters expressed in the brain or the cerebral microvasculature, such as those described supra, including MDR1, MDR3, ABC1, ABC2, ABC3, ABC7, ABC8, MRP4, MRP5 and the human ABC transporters encoded by the ESTs 45597, 122234, 123147, 131042, 157481, 182763, 352188 and 422562. The term "modulate" includes effect(s) on ABC transporters that prevent or inhibit amyloid production and/or release, which may ultimately affect amyloid deposition, e.g., in the context of the therapeutic methods of the invention. In another embodiment, the term modulate includes effects on ABC transporters that enhances amyloid deposition, e.g., increase the production of amyloid in an animal model used to screen drugs for their ability to reduce amyloid deposition. For example, the blocker can affect an ABC transporter's ability to transport Aβ extracellularly from a cell, modulate the cleavage of amyloid precursor protein (APP), and modulate the proteolytic processing of APP. In one embodiment, the ABC transporter blocker is one or more lipophilic agents. In another embodiment, the blocker-acts as a substrate for one or more ABC transporters.

The term "altered expression" includes effects upon the level of expression of either the mRNA or protein which encodes an ABC transporter.

Representative blockers useful in the present invention include, but are not limited to verapamil, desmethoxyverapamil, chloroquine, quinine, chinchonidine, primaquine, tamoxifen, dihydrocyclosporin, yohimbine, corynanthine, reserpine, physostigmine, acridine, acridine orange, quinacrine, trifluoroperazine chlorpromazine, propanolol, atropine, tryptamine, forskolin, 1,9-dideoxyforskolin, cyclosporin, (U.S. Pat. No. 4,117,118 (1978)), PSC-833 (cyclosporin D,6-[(2S, 4R, 6E)-4-methyl-2-(methylamino)-3-oxo-6-octenoic acid]-(9CI)), [U.S. Pat. No. 5,525,590] [ACS 121584-18-7], Keller et al., "SDZ PSC 833, a non-immunosuppressive cylcosporine: its potency in overcoming p-glycoprotein-mediated multidrug resistance of murine leukemia", *Int J Cancer* 50:59314 597 (1992)), RU-486 (17β-hydroxy-11β-[4-dimethylaminophenyl]-17αprop-1-ynyl estra-4,9-dien-3 one), RU-49953 (17β-hydroxy-11β,17α-[4-dimethylaminophenyl]-17αprop-1-ynyl estra-4,9 dien-3 one), S9778 (6-{4-[2,2-di()-ethylamino]-1-piperidinyl}-N,N', di-2-propenyl-1,3,5-triazine-2,4-diamine, bismethane sulfonate, [U.S. Pat. No. 5,225,411; EP 466586] [ACS # 140945-01-3]; Dhainaut et al., "New triazine derivatives as potent modulators of multidrug resistance," *J Medicinal Chemistry* 35:2481–2496 (1992)), MS-209 (5-[3-[4-(2,2-diphenylacetyl)piperazin-1-yl]2-hydroxypropoxy]quinoline sesquifumarate, [U.S. Pat. No. 5,405,843 (continuation of U.S. Pat. No. 5,112,817)], [ACS # 158681-49-3], Sato et al., "Reversal of multidrug resistance by a novel quinoline derivative, MS-209, *Cancer Chemother Pharmacol* 35:271–277 (1995)), MS-073 (Fukazawa et al., European Patent Application 0363212 (1989)), FK-506 (Tanaka et al., M. Physicochemical properties of FK-506, a novel immunosuppressant isolated from *Streptomyces tsukubaensis" Transplantation Proceedings*.

19(5 Suppl 6):11-6, (1987); Naito et al., "Reversal of multidrug resistance by an immunosuppressive agent FK-506," *Cancer Chemother & Pharmacol.* 29:195–200 (1992); Pourtier-Manzanedo et al., "FK-506 (fujimycin) reverses the multidrug resistance of tumor cells in vitro," *Anti-Cancer Drugs* 2:279–83 (1991); Epand & Epand, "The new potent immunosuppressant FK-506 reverses multidrug resistance in Chinese hamster ovary cells," *Anti-Cancer Drug Design* 6:189–93 (1991)), VX-710 (2peperidinecarboxylic acid, 1-[oxo(3,4,5-trimethoxyphenyl)acetyl]-3-(3-pyridinyl)-1-[3 (3-pyridinyl)propyl]butyl ester [ACS 159997-94-1] [U.S. Pat. No. 5,620,971] Germann et al., "Chemosensitization and drug accumulation effects of VX-710, verapamil, cyclosporin A, MS-209 and GF120918 in multidrug resistance-associated protein MRP" *Anti-Cancer Drugs* 8, 141–155 (1997); Germann et al., "Cellular and biochemical characterization of VX-710 as a chemosensitizer: reversal of P-glycoprotein-mediated multidrug resistance in vitro" *Anti-Cancer Drugs* 8, 125–140 (1997)), VX-853 ([U.S. Pat. No. 5,543,423] [ACS # 190454-58-1), AHC-52 (methyl 2-(N-benzyl-N-methylamino)ethyl-2,6-dimethyl-4-(2-isopropylpyrazolo[1,5-a]pyridine-3-yl)-1,4-dihyropyridine-3,5-dicarboxylate; [Japanese Patent 63-135381; European Patent 0270926] [ACS 119666-09-0] Shinoda et al., "In vivo circumvention of vincristine resistance in mice with P388 leukemia using a novel compound, AHC-52," *Cancer Res* 49:1722-6 (1989)), GF-120918 (9,10-dihydro-5-methoxy-9-oxo-N-[4-[2-(1,2,3,4-tetrahydro-6,7-dimethoxyisoquinol-2-yl) ethyl]phenyl]-4 acridinecarboxamide, [U.S. Pat. No. 5,604,237] [ACS # 143664-11-3] Hyafil et al., "In vitro and in vivo reversal of multidrug resistance by GF 120918, an acridonecarboxamide derivative," *Cancer Res* 53:4595–4602 (1993)), and XR-9051 (3-[(3Z,6Z)-6-Benzylidene-1-methyl-2,5-dioxopiperazin-3-ylidenemethyl]-N-[4-[2-(6,7dimethoxy-1,2,3,4-tetrahydroisoquinolin-2-yl)ethyl]phenyl]benzamide hydrochloride, [ACS#57-22-7]).

In a preferred embodiment, blockers useful in the present invention include RU-49953, verapamil, desmethoxyverapamil, cyclosporin, chloroquine, quinine, chinchonidine, primaquine, FK-506, MS-209, MS-073, S 9788, AHC-52, tamoxifen, dihydrocyclosporin, yohimbine, corynanthine, reserpine, physostigmine, acridine, acridine orange, quinacrine, chlorpromazine, propanolol, atropine, tryptamine, forskolin, 1,9-dideoxyforskolin, PSC-833, VX-710, VX-853, GF120918, XR-9051 and trifluoperazine. In another embodiment, blockers useful in the present invention include RU-486, RU-49953, verapamil, desmethoxyverapamil, cyclosporin, chloroquine, quinine, chinchonidine, primaquine, FK-506, MS-209, MS-073, S 9788, AHC-52, tamoxifen, dihydrocyclosporin, yohimbine, corynanthine, reserpine, physostigmine, acridine, acridine orange, quinacrine, chlorpromazine, propanolol, atropine, tryptamine, forskolin, 1,9-dideoxyforskolin, PSC-833, VX-710, VX-853, GF120918, XR-9051 and trifluoperazine. In one embodiment, the ABC transporter blocker is not RU-486. Preferred blockers include PSC 833, MS-209, VX-710, VX-853, GF 120918, XR-9051. S 9788 and RU-49953.

RU-486 is generally associated with steroid hormone receptors such as glucocorticoid and progesterone receptors. For example, RU-486 acts as an antagonist toward these receptors and most commonly is used to block their ability to alter gene transcription (Moguilewsky M. and Philbert D., RU38486: "Potent anti-glucocorticoid activity correlated with strong binding to the cytosolic glucocorticoid receptor followed by impaired activation." *J Steroid Biochem.* 20:271–276(1984); Meyer et al. "Agonistic and antagonistic activities of RU-486 on the functions of the human progesterone receptor." *EMBO J* 9:3923–3932 (1990)). "Steroid hormone receptor agonists and antagonists such as RU-486 are also able to act in a "nongenomic" fashion, altering tyrosine phosphorylation, neurotransmitter release, the concentration of intracellular calcium, inositol triphosphate production, levels of intracellular cAMP, and membrane potential." (Wehling, M. "Nongenomic actions of steroid hormones", *Trends Endocrinol. Metab.* 5:347–353, (1994)). RU-486 also causes dissociation of the hetero-oligomeric complex of proteins to which unliganded steroid hormone receptors are bound resulting in release and activation of steroid hormone receptor associated proteins (Lebeau, M. C. and Baulieu, E. E., Steroid antagonists and receptor-associated proteins, Human Reproduction 9(Suppl)2:11–21 (1994)). Steroid hormone receptors and structurally related antagonists also are known to act upon numerous membrane proteins, in particular neurotransmitter receptors (Brann D. W. et al. Emerging diversities in the mechanism of action of steroid hormones, *J Steroid Biochem. Mol. Biol.* 52:113–133, (1995)).

RU49953 (17b-hydroxy-11b,17a-[4-dimethylaminophenyl]-17a prop-1 ynyl estra-4,9-dien-3 one) is a derivative of the antiglucocorticoid/antiprogestin RU486 (17b-hydroxy-11b-[4-dimethylaminophenyl]-17a prop-1-ynyl estra-4,9-dien-3 one) which does not bind to either glucocorticoid or progesterone receptors to any appreciable degree (Marsaud V, Mercier-Bodard C, LeBihan S, Renoir JM, "Dexamethasone and triamcinoloneacetonide uptake by mouse fibroblasts is differently modulated by the immunosuppressants cyclosporin A, FK506, rapamycin and their analogues, as well as by other P-glycoprotein ligands", *J Steroid Biochem Mol Biol* (in press)), however they do bind to and block MDR 1 mediated efflux (Jault, Renoir, & DiPietro, personal communication cited in Marsaud et al., in press).

The term "disease state" is intended to include those diseases, disorders or conditions which are associated with an increased amount of amyloid deposition, relative to a subject not afflicted with the disease, disorder or condition, in that the deposition of amyloid is directly or indirectly a causative agent of the disease, disorder or condition. The amyloid deposition does not have to be the sole causative agent of the disease, disorder or condition but be merely responsible for causing some of the symptoms typically associated with the disease, disorder, or condition being treated. Amyloid deposition can be the causative agent alone or at least one other agent can be involved in the state being treated. Examples include Alzheimer's Disease, head trauma, stroke, e.g., cerebral ischemia, Down's syndrome, hereditary cerebral hemorrhage amyloidosis, familial Mediterranean Fever, familial amyloid nephropathy with urticaria and deafness [Muckle-Wells syndrome], myeloma or macroglobulinemia, chronic hemodialysis, familial amyloid polyneuropathy, familial amyloid cardiomyopathy, adult onset diabetes, insulinoma, gelsolin, cystatin C (hereditary cerebral hemorrhage with amyloidosis), familial amyloidotic polyneuropathy, Scrapie, Creutzfeldt-Jacob disease, kuru, Gerstmann-Straussler-Scheinker syndrome, bovine spongiform encephalopathy. Preferred examples include those symptoms associated with Alzheimer's Disease, stroke and head trauma The present invention provides methods for treating head trauma by administering to a subject having head trauma an effective amount of at least one ABC transporter or flippase blocker, or a pharmaceutically acceptable salt thereof, such that treatment occurs.

The present also provides methods for treating stroke by administering to a subject affected by a stroke an effective amount of at least one ABC transporter or flippase blocker, or a pharmaceutically acceptable salt thereof, such that treatment occurs.

The term "lipophilic agent," as the term is used herein, refers to a compound, such as a therapeutic agent, which, as a separate entity, is more soluble in nonpolar solvents than water. For example, verapamil is considered lipophilic because it has greater solubility in hexane than in water.

The lipophilic nature of a lipophilic agent is related to its structure. For example, the agent can include lipophilic substituents such as saturated or unsaturated, substituted or unsubstituted alkyl, aryl or heteroaryl groups. Such groups include substituted and unsubstituted, normal, branched or cyclic alkyl groups having 3 or more carbon atoms, substituted or unsubstituted arylalkyl or heteroarylalkyl groups and substituted or unsubstituted aryl or heteroaryl groups.

Further, the lipophilic nature of the therapeutic agent can also be attributed to the "backbone" of the compound. The backbone of the compound is that portion of the structure to which substituents are attached and can include lipophilic groups such as steroidal groups, saturated or unsaturated, substituted or unsubstituted alkyl, aryl or heteroaryl groups, or other fused cyclic ring systems.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In one embodiment, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, cycloalkyls have from 4–10 carbon atoms in their ring structure, and more preferably have 5, 6 or 7 carbons in the ring structure.

Moreover, the term alkyl as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxy alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl (e.g., phenylmethyl (benzyl)).

The term "aryl" as used herein includes 5- and 6-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, aralkyl, or an aromatic or heteroaromatic moiety. Aryl groups can also be fused or bridged with alicyclic or heterocyclic rings which are not aromatic so as to form a polycycle (e.g., tetralin).

Unless the number of carbons is otherwise specified, "lower alkyl" as used herein means an alkyl group, as defined above, but having from one to ten carbons, more preferably from one to six carbon atoms in its backbone structure. Preferred alkyl groups are lower alkyls having one to three carbon atoms.

The terms "heterocyclyl" or "heterocyclic group" refer to 3- to 10-membered ring structures, more preferably 4- to 7-membered rings, which ring structures include one to four heteroatoms. Heterocyclyl groups include pyrrolidine, oxolane, thiolane, oxazole, piperidine, piperazine, morpholine, lactones, lactams such as azetidinones and pyrrolidinones, lactones, sultams, sultones, and the like. The heterocyclic ring can be substituted at one or more positions with such substituents as described above, as for example, halogen, hydroxyl. alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, aralkyl, or an aromatic or heteroaromatic moiety. A heteroalkyl moiety is an alkyl substituted with a heteroaromatic group.

The terms "polycyclyl" or "polycyclic group" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyj, alkoxycarbonyl, arninocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, aralkyl, or an aromatic or heteroaromatic moiety.

The term "substrate" as used herein means the specific compound acted upon by an enzyme, transporter, or other cellular proteins.

The language "modulation of amyloid deposition" as used herein, means that amyloid deposition is prevented or decreased, e.g. Aβ deposition. This modulation can be by one or more chemically induced physiological mechanisms. For example, the blocking agents and/or the lipophilic agents of the present invention can modulate amyloidosis in a subject such as by acting as an ATP binding cassette (ABC) transporter blocker, more preferably as a blocker of an ABC transporter expressed in the brain or cerebral microvasculature as described supra. For example the blockers and/or the lipophilic agents of the present invention can modulate the cleavage of amyloid precursor protein (APP). In one embodiment the blocker and/or lipophilic agent can modulate proteolytic processing of APP, thereby decreasing production of amyloid-β protein (Aβ). In yet another embodiment, the blockers and/or the lipophilic agents of the present invention modulate proteolytic processing of $APP_S$ thereby increasing production of soluble amyloid precursor protein ($APP_S$). Additionally, the blockers and/or lipophilic agents of the present invention can modulate an ABC transporter's ability to export Aβ from a cell. Most preferably, the blockers and/or lipophilic agents of the present invention inhibit or prevent export of Aβ from a cell.

Alternatively, the term "modulate" is intended to mean that amyloid deposition is increased, e.g. Aβ deposition. This modulation can be induced by one or more chemically induced physiological mechanisms. For example, effective amounts of a chemical agent can be screened for increased amyloid deposition in a subject. The increase can be evaluated by comparing a subject treated with an agent of the present invention to a similar subject who was not treated. Furthermore, in some embodiments of the invention, the subject can have pre-existing amyloid deposits; therefore, the chemical agent serves to enhance the existing deposits. Preferably the increase is at least about 20%, more preferably by at least about 40%, even more preferably by at least about 60%, and still more preferably by at least about 80% relative to an untreated subject.

The term "subject" is intended to include mammals having amyloid deposition, including one or more amyloid related symptoms, or which are susceptible to amyloid deposition. Examples of such subjects include humans, dogs, cats, pigs, cows, horses, rats and mice.

The term "administering" is intended to include routes of administration which allow the ABC transporter blocker and/or the lipophilic agent to perform its intended function, e.g., preventing or inhibiting amyloidosis. A variety of routes of administration are possible including, but not necessarily limited to parenteral (e.g., intravenous, intraarterial, intramuscular, subcutaneous injection), oral (e.g., dietary), topical, nasal, rectal, or via slow releasing microcarriers depending on the disease or condition to be treated. Oral, parenteral and intravenous administration are preferred modes of administration. Formulation of the compound to be administered will vary according to the route of administration selected (e.g., solution, emulsion, gels, aerosols, capsule). An appropriate composition comprising the compound to be administered can be prepared in a physiologically acceptable vehicle or carrier and optional adjuvants and preservatives. For solutions or emulsions, suitable carriers include, for example, aqueous or alcoholic/aqueous solutions, emulsions or suspensions, including saline and buffered media, sterile water, creams, ointments, lotions, oils, pastes and solid carriers. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See, generally, *Remington's Pharmaceutical Science*, 16th Edition, Mack, Ed. (1980)).

The language "effective amount" is that amount of the blocker which allows it to perform its intended function. For example, an effective amount is that amount sufficient to inhibit, partially or totally, amyloid release, production and/or deposition or to reverse amyloid deposition or prevent or reduce its further deposition. The "effective amount" also includes the amount sufficient to treat amyloidosis or Alzheimer's disease. The effective amount will depend upon a number of factors, including biological activity of the blocker and/or lipophilic agent, age, body weight, sex, general health, severity of the disease to be treated, as well as appropriate pharmacokinetic properties. For example, dosages of the active substance can be from about 10 mg/kg/day to about 1000 mg/kg/day. A therapeutically effective amount of the active substance can be administered by an appropriate route in a single dose or multiple doses. Further, the dosages of the active substance can be proportionally increased or decreased as indicated by the exigencies of the therapeutic or prophylactic situation.

The term "amyloidosis" is art recognized and is intended to include amyloid deposition related symptoms, such as progressive and undesirable memory impairment, loss of language and visuospatial skills, and behavior deficits. These changes in cognitive function are likely the result of degeneration of neurons in the cerebral cortex, hippocampus, basal forebrain, and other regions of the brain. The presence of large numbers of neurofibrillary tangles in degenerated neurons, neuritic plaques in the extracellular space and in the walls of the cerebral microvasculature are thought to be a result of amyloid deposition. For example, neuritic plaques consist of deposits of proteinaceous material surrounding an amyloid core.

The language "pharmaceutically acceptable salt" is intended to include pharmaceutically acceptable salts capable of being solvated under physiological conditions. Examples of such salts include sodium, disodium, potassium, dipotassium, and hemisulfate. The term is further intended to include lower hydrocarbon groups capable of being solvated under physiological conditions, e.g. alkyl esters, methyl, ethyl and propyl esters.

The present invention further pertains to packaged pharmaceutical compositions for treating amyloidosis. The package includes a container for holding an effective amount of a pharmaceutical composition and instructions for using the pharmaceutical composition for treatment of amyloidosis. The pharmaceutical composition includes at least one ABC transporter blocker for modulating amyloid deposition in a subject.

The term "pharmaceutical composition" includes blockers and/or lipophilic agents of the present invention and includes ingredients, such as other therapeutically active substances, inert ingredients, and carrier compounds. The components of the composition must be compatible, meaning that the components must be capable of being commingled with the active substance, e. g. the blocker and/or the lipophilic agent and with each other in a manner such that there is no interaction which would substantially reduce during use the composition's efficacy for modulating amyloid deposition.

The pharmaceutical compositions can be prepared by known procedures using well known and readily available ingredients. In making the pharmaceutical compositions of the present invention, the active substance will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing up to 10% by weight of the active compound, soft and hard gelatin capsules, packaged powders, and the like. Examples of suitable carriers, excipients, and diluents are lactose, dextrose, sucrose, sorbitol, mannitol, starches, gumacacia, calcium phosphate, alginates, tragacanth, gelatin, calcium silicate, microcrystalline cellulose, polyvinylpyrrolidone, cellulose, water syrup, methyl cellulose, methylhydroxybenzoates, propylhydroxybenzoates, propylhydroxybenzoates, talc, and other compounds as are well known to those skilled in the pharmaceutical arts.

Blockers and/or lipophilic agents of the invention can be administered alone or in conjunction with other pharmacologically active agents, e.g., together with immunosuppressive agents or together with antibiotics and/or antiviral agents. Compounds that can be coadministered include steroids (e.g. methyl prednisolone acetate), NSAIDs and other known immunosuppressants such as azathioprine, 15-deoxyspergualin, mizoribine, mycophenolate mofetil, brequinar sodium, leflunomide, and related molecules. Dosages of these drugs will also vary depending upon the condition and individual to be treated.

Blockers and/or lipophilic agents of the invention can be administered prior to the onset of amyloidosis, or after the onset of amyloidosis. The blockers and/or lipophilic agents also can be administered as a prodrug which is converted to another form in vivo.

The present invention also pertains to methods for identifying agents which modulate amyloid production in an organism by administering to an organism, e.g., a transgenic mouse model which overexpresses Aβ, resulting in amyloid deposits, an effective amount of at least one ATP binding cassette (ABC) transporter blocker, such that modulation of amyloid deposition occurs. The observation that amyloid production, release or deposition occurs in membrane vesicles, cells, or organisms is used to identify the agents. In another embodiment of the present invention, either the ABC transporter blocker or another agent induces a change in ABC transporter expression or stability which enhances amyloid production and can be used to produce a model for amyloidosis; in one embodiment, the model is an animal model, although other organisms, cell lines and even membranes may be useful in this regard. These models can be used to screen agents or drugs for their ability to reduce or prevent amyloid deposits.

The term "organism" is intended to include single cells, such as E. coli, multicellular organisms such as yeast and C. elegans cell lines and multicellular organisms including mammals, such as mice, rats, guinea pigs, and pigs that can develop amyloidosis. Examples of suitable multicellular organisms include transgenic animals, e.g., mammals, as well as those mammals identified as capable of developing amyloidosis, e.g., having amyloid deposition.

The term "method for identifying agents" includes assays and the like suitable for determining what agent or agents (blockers and/or lipophilic agents) elicit a response by the assay method. For example, combinatorial libraries can be screened to determine whether any members of the library have a desired activity, and, if so, to identify the active species. Methods of screening combinatorial libraries have been described (see, e.g., Gordon et al., *J Med. Chem.*, op. cit.). Soluble compound libraries can be screened for modulating transport of amyloid across cell membrane, followed by identification of the isolated compounds by conventional techniques (e.g., mass spectrometry, NMR, and the like). Preferably, the library compounds are conjugated to a label (e.g., fluorophores, colorimetric enzymes, radioisotopes, luminescent compounds, and the like) that can be detected to indicate reduction in ABC transport of amyloid. Alternatively, immobilized compounds can be selectively released and allowed to interact with an ABC transporter. Exemplary assays useful for screening the libraries of the invention are known in the art (see, e.g., E. M. Gordon et al., *J. Med. Chem.* 37:1385–1401 (1994)).

For example, cell lines can be developed which overexpress each member of the family of ABC transporters, preferably, those ABC transporters expressed in the brain and/or the cerebral microvasculature, e.g., MDR1, MDR3, ABC1, ABC2, ABC3, ABC7, ABC8, MRP4, MRP5 and the human ABC transporters encoded by the ESTs 45597, 122234, 123147, 131042, 157481, 182763, 352188 or 422562, thereby providing surfaces of such cells with thousands of copies of a particular ABC transporter (For similar techniques see: Shapiro, A. B. and Ling, V., Reconstitution of Drug Transport by Purified P-Glycoprotein, *Journal of Biological Chemistry*, 270: 16167–16175, (1995)). From these cells, inside-out plasma vesicles can be constructed, thereby externalizing all of the molecular architecture found inside cells. Addition of ATP to these vesicles, causes the ABC transporter to move substrates across the cell membrane, except rather than moving substrates from inside (intracellular) to outside (extracellular), the substrate now becomes concentrated inside the vesicle. Reliable preparations of plasma vesicles that transport amyloid can be used to screen chemical libraries to isolate new compounds capable of reducing ABC transport of amyloid.

The present invention further pertains to in vitro and in vivo methods for identifying agents which modulate transport of amyloid across membranes, e.g., cellular or synthetic membranes. The methods include introducing an agent into a model system which contains a membrane, an ABC transporter expressed in the brain or cerebral microvasculature and amyloid. The ability of the agent to modulate the transport of amyloid across the membrane is measured. Suitable synthetic membranes are those composed of lipids as described in (Slatin, S. "Colicin E in planar lipid bilayers" *Internat. J Biochem.* 20:737–744 (1988); Krasilnikov et al., "A novel approach to study the geometry of the water lumen of ion channels: colicin 1 a in planar lipid bilayers" *J Memb. Biol.* 161:83–92(1998)).

The present invention also pertains to in vitro methods for inserting ABC transporters, preferably those ABC transporters expressed in the brain and/or cerebral microvasculature, e.g., MDR1, MDR3, ABC1, ABC2, ABC3, ABC7, ABC8, MRP4, MRP5 and the human ABC transporters encoded by the ESTs 45597, 122234, 123147, 131042, 157481, 182763, 352188 or 422562, into planar lipid bilayers as a means of assaying regulation of amyloid transport. For example, purified or recombinant proteins can be inserted into planar lipid bilayers (Slatin, S. "Colicin E in planar lipid bilayers" *Internat. J Biochem.* 20:737–744 (1988); Krasilnikov et al., "A novel approach to study the geometry of the water lumen of ion channels: colicin 1 a in planar lipid bilayers" *J Memb. Biol.* 161:83–92 (1998)) such that transport of amyloid across the planar lipid bilayer by the ABC transporter can be measured. The methods include introducing an agent into a model system which contains a planar lipid bilayer, an ABC transporter and amyloid. The ability of the agent to modulate the transport of amyloid across the planar lipid bilayer can be measured.

The term "model system" includes cells, cell lines, mammals, birds, insects, single- and multicellular organisms and in vitro systems.

The following discussion, which is not to be construed as limiting on the invention in any way, but is presented for purposes of illustration, describes a plausible mechanism for the modulation of cellular trafficking and proteolytic processing of APP.

Immature APP is believed to be transported through intracellular secretory machinery to the membrane where it is found as a transmembrane protein known as mature APP. During this maturation process, APP can be cleaved by β- and γ-secretases; the cleavage occurs at the N- and C-termini of Aβ (respectively), resulting in production of Aβ peptide. Once at the membrane, mature APP undergoes one of several proteolytic processing routes. The a-secretory processing of APP involves cleavage of the molecule in the extracellular domain, near the membrane and within the Aβ sequence. This cleavage of APP has two potential consequences: (1) it precludes formation of Aβ; and (2) solubilizes the extracellular domain of APP which is then released into the extracellular space. An alternative route involves internalization to an endosomal compartment with potential for β- and γ-secretase cleavage, once again resulting in production of Aβ.

It is also believed that certain ABC transporters export Aβ from cells. MDR1, MDR3, ABC1, ABC2, ABC3, ABC7, ABC8, MRP4, MRP5 and the human ABC transporters encoded by the ESTs 45597, 122234, 123147, 131042, 157481, 182763, 352188 or 422562 are members of the ATP-binding cassette (ABC) superfamily of transporters; using ATP as an energy source, certain ABC transporters such as MDR1 are known to pump various molecules against their concentration gradients (Endicott, J. A. and V. Ling, "The biochemistry of P-glycoprotein-mediated multi-drug resistance", *Annu. Rev. Biochem.* 58:137–171 (1989); Gottesman, M. M. and I. Pastan, "Biochemistry of multidrug resistance mediated by the multidrug transporter", *Alinu. Rev. Biochem.* 62:385–342 (1993), the teachings of which are hereby incorporated by reference). In humans, two isoforms of p-glycoprotein exist; only one of them, termed MDR1, confers the multidrug resistance phenotype. In this document, the term p-glycoprotein is used to indicate the MDR1 gene product. Other isoforms of p-glycoprotein as well as other members of the superfamily of ABC transporters can also serve to transport Aβ from cells, and therefore can also be targets for the drugs listed below as "active compounds". A wide assortment of drugs act as substrates for MDR1; while structurally unrelated, all share the property of being exceedingly hydrophobic (Zamora, J. M. et al., "Physical-chemical properties shared by compounds that modulate multidrug resistance in human leukemia cells", *Mol. Pharmacol.* 33:454–462 (1988), the teachings of which are hereby incorporated by reference) which has led to the belief that MDR1 act as either a "hydrophobic vacuum cleaner" for a wide variety of membrane-associated hydrophobic molecules or as a flippase (Higgins, C. F. and M. M. Gottesman, "Is the multidrug transporter a flippase?", *TIBS* 17:18–21 (1992), the teachings of which are hereby incorporated by reference). Among the molecules which can be exported are lipophilic peptides (Raymond, M. et al., "Functional complementation of yeast ste6 by a mammalian multidrug resistance mdr gene", *Science* 256:232–234; Sharma, R. C. et al. "Peptide transport by the multidrug resistance pump", *J Biol. Chem.* 267:5731–5734 (1992), the teachings of which are hereby incorporated by reference). Because Aβ is a small, lipophilic peptide, it has appropriate properties to act as a substrate for MDR1.

The term "flippase" is art recognized and is intended to include the ability of an ABC transporter to act as a flipping agent, e.g., to move Aβ from the inner leaflet of a lipid bilayer to the outer leaflet. That is, an ABC transporter acting as a flippase delivers Aβ to the outer leaflet of the lipid bilayer, in this scenario, other molecules may be involved in moving Aβ from the outer leaflet of the lipid bilayer into the extracellular space. However, the flippase action of the ABC transporter is critical to the multi-factorial process leading to Aβ efflux.

The term "flippase blocker" is intended to include those compounds that can modulate ABC transporters expressed in the brain or the cerebral microvasculature, such as those described supra, including MDR1, MDR3, ABC1, ABC2, ABC3, ABC7, ABC8, MRP4, MRP5 and the human ABC transporters encoded by the ESTs 45597, 122234, 123147, 131042, 157481, 182763, 352188 or 422562.

The sequence similarities between MDR1 and other members of the superfamily of ABC transporters (Dean and Allikmets, "Evolution of ATP-binding cassette transporter genes" *Curr Opin Genetics Dev* 5:779–785 (1995)) suggest that they too may modify Aβ efflux from cells. This is a reasonable inference, given what is known about the function of members of the family which are already characterized. For example, the yeast ABC transporter known as ste-6 is responsible for export of a peptide called a-factor: yeast which are deficient in ste6 lack a-factor export, but replacement of ste-6 with either the ABC transporter mdr3, a mouse homologue of human MDR1 (Raymond et al., "Functional complementation of yeast ste6 by a mammalian multidrug resistance mdr gene" *Science* 256:232–234 (1992)) or the human ABC transporter MRP1 (Ruetz et al., "Functional expression of the multidrug resistance-associated protein in the yeast Saccharomyces cerevisiae" *J Biol Chem* 271:4154–4160 (1996)) restores a-factor export. These data demonstrate (a) that multiple members of the family indeed act as transporters; and (2) that the substrates which they transport are not unique to any given family member. Further evidence for the notion that ABC transporters indeed function as transporters in cells include the observation that the human MDR3 gene product promotes translocation of phosphatidylcholine (Smith et al., "The human MDR3 p-glycoprotein promotes translocation of phosphatidylcholine through the plasma membrane of fibroblasts from transgenic mice" *FEBS Left* 354:263–266 (1994)), that the ABC transporter known as abc1 appears to be involved in secretion of interleukin 1β (Hamon et al., "Interleukin-1β secretion is impaired by inhibitors of the ATP binding cassette transporter, ABC1," *Blood* 90:2911–2915 (1997)), and that the transport of certain peptides into the lumen of the endoplasmic reticulum is accomplished by the conjoint efforts of two members of the ABC transporter family known as TAP1 and TAP2 (Heemels MT and Ploegh H, "Generation, translocation, and presentation of MHC class I-restricted peptides." *Ann Rev Biochem.* 64:463–91 (1995)).

Aβ is released from all cells, and thus it is reasonable to assume that all cells have a mechanism for Aβ release. In cells expressing MDR1, it is believed that this ABC transporter is involved in the process of Aβ efflux. However, other than the microvasculature, there is little or no MDR1 expression in the brain, yet neurons produce and release prodigious amounts of Aβ (Busciglio et al., "Generation of β-amyloid in the secretory pathway in neuronal and non-neuronal cells," *Proc Natl Acad Sci USA* 90:2092–2096 (1993); Simons et al., "Amyloidogenic processing of the human amyloid precursor protein in primary cultures of rat hippocampal neurons," *J Neurosci* 16:899–908 (1996)). Thus, it seems reasonable to propose that other ABC transporters are involved in the process of Aβ efflux in brain. As amyloid deposition in Alzheimer's disease occurs both in the parenchyma of the brain and in the microvasculature (Selkoe, DJ "The molecular pathology of Alzheimer's disease," *Neuron* 6:487–98 (1991)), ABC transporters expressed in brain and the microvasculature represent key targets for regulating Aβ release via the present invention. Thus, brain-and microvasculature expressing ABC transporters represent preferred targets for the development of Alzheimer's disease therapeutics.

It is also possible that the ABC transporters MDR1, MDR3, ABC1, ABC2, ABC3, ABC7, ABC8, MRP4, MRP5 and the human ABC transporters encoded by the ESTs 45597, 122234, 123147, 131042, 157481, 182763, 352188 or 422562 can function to allosterically modify the function of other membrane proteins. In some cells, modulation of p-glycoprotein by ABC transporter blockers has been shown to alter the magnitude of volume-activated chloride currents (reviewed in Higgins, C. F. Volume-activated chloride currents associated with the multidrug resistance P-glycoprotein, *J Physiol.* 482:31S–36S (1995)). In this model, p-glycoprotein and other ABC transporters have multiple functions, one of which is to allosterically modify the function of the other membrane proteins. The present invention is consistent with a model in which allosteric modification of other membrane proteins by an ABC transporter is responsible for the change in APP catabolism, such that Aβ release is reduced, and/or in which the ABC transporter exports Aβ. From this, it follows that pharmacological agents which alter the ability of these molecules to export Aβ or the expression of such molecules can be therapeutically useful in Alzheimer's disease.

The invention is further illustrated by the following examples which in no way should be construed as being further limiting. The contents of all references, pending patent applications and published patent applications, cited throughout this application are hereby incorporated by reference. It should be understood that the animal cell line models used throughout the examples are accepted cell models and that the demonstration of efficacy in these cell models is predictive of efficacy in humans.

EXEMPLIFICATION

I. The Use of a P-glycoprotein Blocker For Increasing $APP_S$ Secretion

Murine nerve growth factor (NGF) was purchased from GIBCO and dexamethasone (DEX) was purchased from SIGMA. Mifepristone (RU-486) was purchased from Research Biochemicals International (RBI, Natick, Mass.) through the NIMH (National Institute for Mental Health) Chemical Synthesis Program. Cyclosporin A (CsA) was purchased from RBI. The Anti-Alzheimer Precursor Protein A4 (22C 11) monoclonal antibody specific to the pre-A4 molecule (amyloid precursor protein) was purchased from Boehringer Mannheim.

The GSrasDN1 PC12 subline (Dr. Simon Halegous (State University of New York at Stony Brook)) expressing the dominant inhibitory mutant ras gene, $p21^{N17}$ under the control of a dexamethasone-inducible MMTV promoter (mouse mammary tumor virus), obtained as a gift from Dr. Simon Halegoua, (Kremer et al., *J. Cell Biol.* 115(3):809–819 (1991)) and grown in Dulbecco's modified Eagles' medium (DMEM, GIBCO) containing 5% fetal bovine serum (FBS: v/v) and 10% heat inactivated horse serum (HS, GIBCO).

RU-486 and NGF were solubilized in dimethylsulfoxide (DMSO). DMSO was used as a control vehicle in all experiments.

For drug exposure experiments in GSrasDN1 PC12 cells, cells were grown to confluence in 75 cm2 polypropylene culture flasks from Falcon. Twelve hours prior to drug treatment, the culture medium was aspirated using a pasteur pipette and replaced with 10 ml of DMEM supplemented with 15% charcoal-stripped calf serum (SIGMA) to remove complement, immunoglobulins and endogenous steroid hormones secreted from the cells. Twelve hours later, this supplemental medium was aspirated and replaced with 10 ml of DMEM containing the treatment drugs. Flasks were allotted into the following treatment groups: a) Control and b) RU-486 (3.0 µM). DMSO concentrations were normalized to 0.06% (v/v) in all flasks.

Twelve hours following drug exposure, the medium was again aspirated and the cells were washed once with 10 ml of phosphate-buffered saline (PBS, SIGMA). Cells were removed from the bottom of the flask by incubating with 1.0 ml of trypsin (GIBCO) for five minutes. 1.0 ml of DMEM was added to the flask, cells were titurated with a pasteur pipette and collected into a 15 ml conical polypropylene tube (Falcon). 10 ml of DMEM was added to the tube and cells were spun-down on a table-top swing-arm centrifuge for 30 seconds. The medium was aspirated and replaced with 2 ml of DMEM. The resultant cell pellet was resuspended first using a 20½ gauge needle followed by a 22½ gauge needle. 8 ml of DMEM was added to make a final volume of 10 ml. 13 µl of this cell suspension was taken for cell counting using a haemocytometer. A dilution was performed using DMEM to make a final cell suspension with a density of $1.0 \times 10^6$ cells/ml. 10 mls of cells from each treatment group was pipetted into 15 ml conical tubes labeled CONTROL, NGF, or RU-486. Drugs were reintroduced to the cells at the same concentration as described above for the 12-hour pretreatment. NGF (50 ng/ml) was added to the tube of cells labeled 'NGF' as a positive control. 1.0 ml of cells from each group was pipetted into appropriately labeled 1.5 ml eppendorf tubes (BIORAD) and placed into a 5% $CO_2$ incubator equilibrated at 37° C. for fifteen minutes.

After the fifteen minutes had elapsed, the tubes were placed immediately on ice to stop any reactions and 200 µl of a protease cocktail (100 µM PMSF (phenylmethanesulfonyl fluoride), 5 µg/ml Leupeptin, 5 µg/ml Aprotinin, and 5 µg/ml Pepstatin) was added to each tube. Cells were pelletted at 14,000 rpm for five minutes at 4° C. and the medium was removed and collected into fresh, ice-cold 1.5 ml eppendorf tubes containing protease inhibitor cocktail. Cell pellets were lysed using 50 µl of met/lysis buffer (10 mM Tris-HCl, 150 mM NaCl, 1% Nonindet P40 (v/v), and 1% Na deoxycholate (w/v), pH 7.4). The nuclear fraction was pelletted down at 14,000 rpm for ten min. and 5 µl of cellular homogenate was collected for a protein quantification.

$APP_S$-containing medium was desalted using ultrafree-CL centrifugation filters with a 30,000 MW cut-off range membrane (Millipore). The desalted supernatant was placed in 1.5 ml eppendorf tubes and concentrated using a speed vac-concentrator. 30 μl of Laemmli sample buffer (0.0625 Tris-HCL, 2% SDS, 10% glycerol, 5% 2-mercaptoethanol, 0.002% bromophenol blue) was added to reconstitute the pellet.

A bicinchoninic acid (BCA) protein assay kit from Pierce (PO Box 117, Rockford, Ill., 61105) was used to perform protein quantification on the cellular extracts. 5 μl of each sample was taken for measurements, according to manufacturer's instructions.

Secreted protein corresponding to 10 μg of cellular protein from each treatment group were boiled at 100° C. for four minutes and separated by tris-glycine SDS-PAGE (sodium dodecyl suflate-polyacrylamide gel electrophoresis). Protein bands were transferred onto nitrocellulose membranes and Western blotting using the 22C11 monoclonal antibody (monoclonal antibody against APP) was performed (Mills, J. and P. B. Reiner, "Phorbol esters but not the cholinergic agonists oxotremorine-M and carbachol increase release of the amyloid precursor protein in cultured rat cortical neurons", *J Neurochem.* 67:1511–1518 (1996). Bands were visualized using an enhanced chemiluminescence "ECL" kit from Amersham Canada Limited, Oakville, Ontario and detected on ECL Hyperfilm (Amersham). Protein bands were quantified by densitometry of the films. $APP_S$ usually ran as two or three close bands on the gel corresponding to the different isoforms of $APP_S$ and they were quantified together and denoted $APP_S$.

Figure 2:
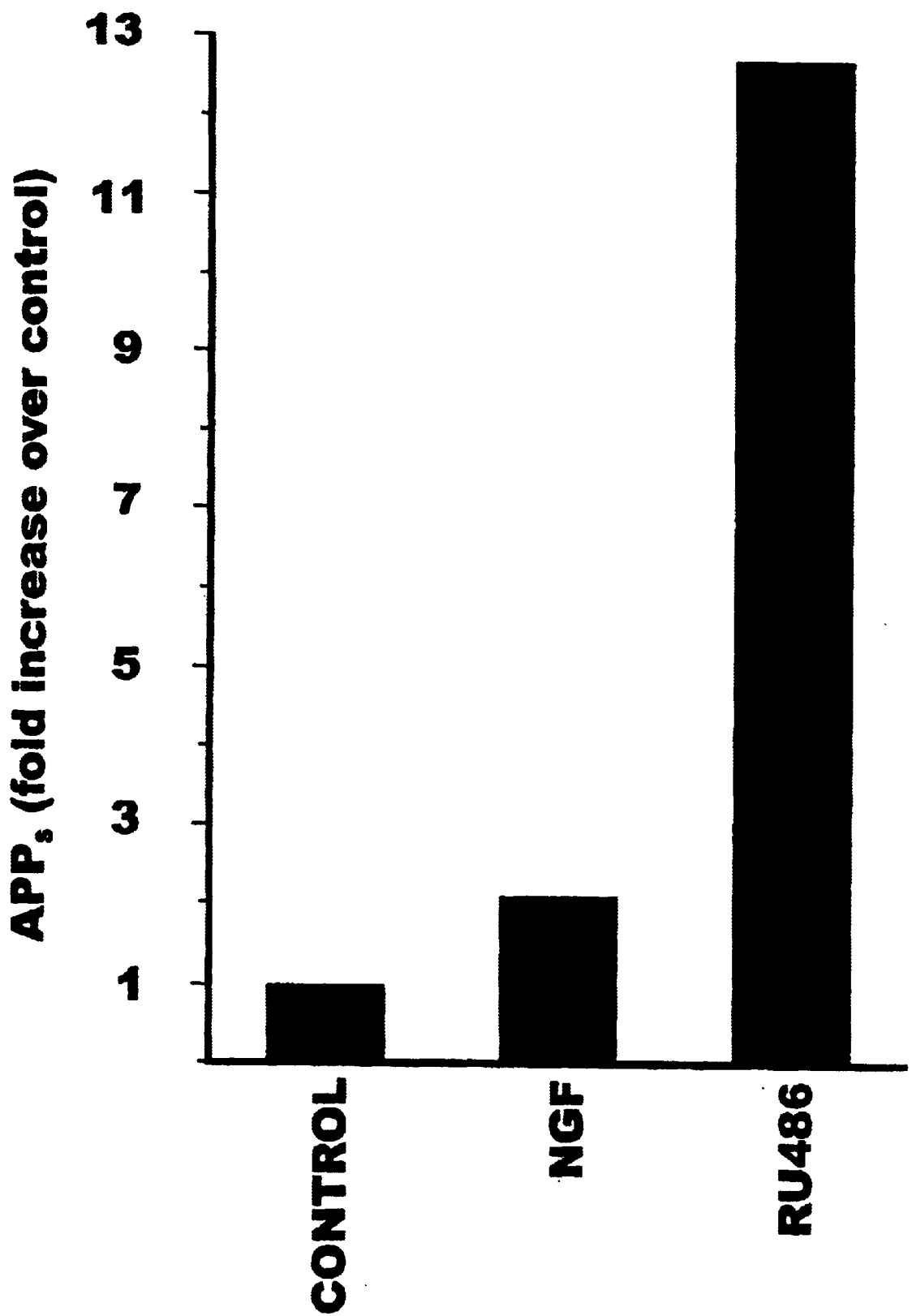
FIG. 2 is a graph comparing the effects of RU-486 and nerve growth factors upon $APP_S$ release from PC12 cells.

RU-486 increased $APP_S$ in the GSrasDN1 PC12 cells (FIG. 1). This cell line was used to examine the role of ras in regulating $APP_S$ secretion. RU-486 was used as a negative control group for the expression of the glucocorticoid-inducible MMTV promoter-linked dominant negative ras gene product in these cells. In these experiments, the effects of prolonged exposure of RU-486 (twelve hours) on these cells were studied and $APP_S$ was collected for fifteen minutes. NGF is a known enhancer of $APP_S$ secretion in PC12 cells (Fukuyama, R. et al., "Nerve growth factor-induced neuronal differentiation is accompanied by differential induction and localization of the amyloid precursor protein (APP) in PC12 cells and variant PC12S cells", *Mol. Brain Res.* 17:17–22 (1993); Haring, R. et al., "NGF promotes amyloid precursor protein secretion via muscarinic receptor activation", *Biochem. Biophys. Res. Comm.* 213:15–23 (1995), the teachings of which are hereby incorporated by reference) and was used as a positive control in this study. The increase in $APP_S$ secretion due to RU-486 was found to be ~12.5-fold increase over control samples and ~6 fold increase over NGF (FIG. 2).

The evidence demonstrates that blockade of p-glycoprotein increases $APP_S$ release from cells. It is art recognized that when release of $APP_S$ is increased that the release of Aβ is decreased (Buxbaum et al., Protein phosphorylation inhibits production of Alzheimer amyloid β//a4 oeotudem *Proc. Natl. Acad Sci.* 90:9195–9198 (1993); Fukushima et al., Activation of the secretory pathway leads to a decrease in the intracellular amyloidongenic fragments generated from the amyloid protein precursor, *Biochem. Biophys. Res. Comm.* 194:202–207 (1993); Gabuzda et al., Inhibition of β-amyloid production by activation of protein kinase C., *J Neurochem.*61:2326–2329 (1993); Hung et al., Activation of protein kinase C inhibits cellular production of the amyloid β-protein, *J Biol. Chem.* 268:22959–22962 (1993); Jacobsen et al., The release of Alzheimer's disease β-amyloid peptide is reduced by phorbol treatment, *J Biol. Chem.* 269:8376–8382 (1994); Wolf et al., Muscarinic regulation of Alzheimer's disease amyloid precursor protein secretion and amyloid β-protein production in human neuronal NT2N cells, *J Biol. Chem.* 270:4916–4922 (1995)).

II. Concentration Effects of RU-486 On $APP_S$ Generation

The materials and methods used herein are as described in Example 1. Various concentrations of RU-486 were used to treat GSrasDN1 PC12 cells. Cells were exposed to final concentrations of 3.0 to 3000.0 nM of RU-486. Drug exposure protocol was carried-out as previously described. Determination of the concentration and quantification of $APP_S$ was also performed as previously described.

Figure 3:
FIG. 3 is a western blot of an SDS-PAGE gel demonstrating that RU-486 increases release of $APP_S$ from PC12 cells in a dose-dependent manner.
Figure 4:
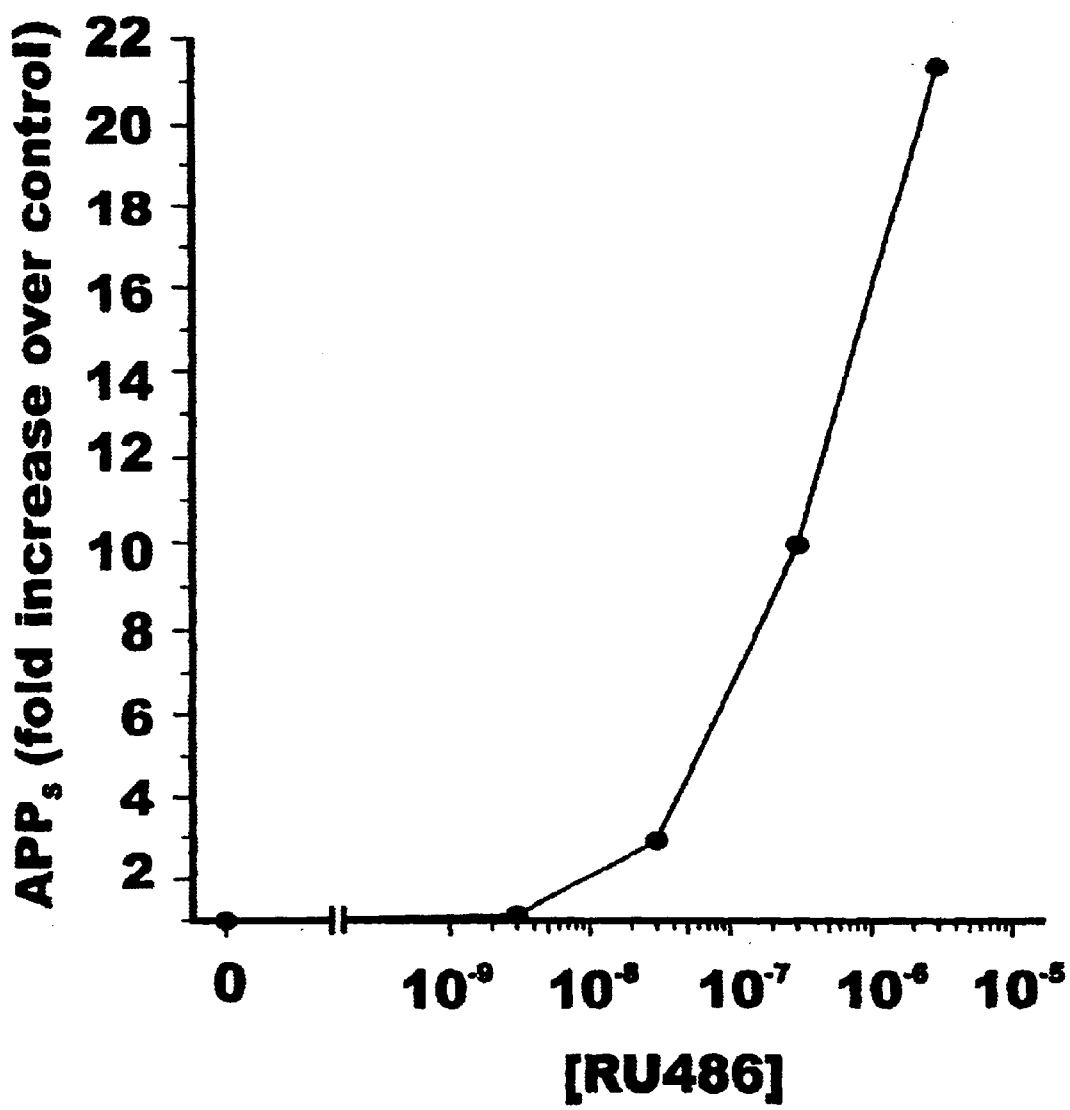
FIG. 4 is a graph showing the dose-dependent effects of RU-486 administration upon $APP_S$ release from PC12 cells.

Results indicated that increased $APP_S$ secretion in GSrasDN 1 PC12 cells is RU-486 dose-dependent (FIG. 3), with a half-maximal effect at about 0.5 μM (FIG. 4). Concentration effect studies above 3.0 μM RU-486 became difficult because RU-486 did not remain a homogenous aqueous solution above that concentration. However, even at sub-maximal concentrations of RU-486, increased $APP_S$ secretion is noted (~21 fold at 3.0 μM RU-486, FIG. 4).

III. The Use of a Second P-glycoprotein Blocker

Phorbol 12-myristate 13-acetate (PMA) was purchased from LC Service Corp., Woburn, Mass. All other materials were obtained as previously described in Example 1. Wild-type PC12 cells were purchased from the American Type Tissue Culture Collection #CRL-1721 and grown in DMEM with 5% FBS fetal bovine serum and 10% horse serum (GIBCO).

PC12 cells grown to confluence were pretreated for twelve hours in DMEM supplemented with charcoal-stripped calf serum (SIGMA) as described above. After pretreatment, cells were trypsinized, resuspended, and counted as described above. 10 mls each of $1.0 \times 10^6$ cells/ml PC12 cells were aliquoted into 15 ml conical tubes containing the appropriate treatment group. PMA was used as a positive control as previous experiments had shown that such treatment increases $APP_S$ release (Buxbaum, J. D. et al., "Processing of Alzheimer β/A4 amyloid precursor protein: Modulation by agents that regulate protein phosphorylation", *Proc. Natl. Acad. Sci. USA* 87:6003–6006 (1990); Caporaso, G. L. et al., "Protein phosphorylation regulates secretion of Alzheimer β/A4 amyloid precursor protein", *Proc. Natl. Acad Sci. USA* 89:3055–3059 (1992); Mills, J. and P. B. Reiner, "Phorbol esters but not the cholinergic agonists oxotremorine-M and carbachol increase release of the amyloid precursor protein in cultured rat cortical neurons", *J Neurochem.* 67:1511–1518 (1996), the teachings of which are hereby incorporated by reference). The final percentage of DMSO in all treatment groups was normalized. to. 0.01% (v/v).

Treatment groups were as follows: a) Control; b) PMA (0.1 μM); c) RU-486 (0.1 μM). The concentration of (0.1 μM) RU-486 was chosen because it was near the $EC_{50}$ mark (FIG. 4). 1.0 ml of each treatment group was pipetted into 1.5 eppendorf tubes and incubated at 37° C. in a 50% $CO_2$ incubator for fifteen minutes. Harvesting and concentration of $APP_S$ were performed as described in Example 1. Protein band separation on SDS-PAGE, visualization of bands, and quantification of $APP_S$ were also performed as previously described.

RU-486 increased $APP_S$ secretion in wild-type PC12 cells following fifteen minute exposure (FIG. 5). The data indicated that the effect previously shown was not due to an effect caused by the presence of the dominant-negative ras gene in the GSrasDN 1 PC12 cell line. Since it is generally accepted that genomic effects of steroid hormone receptor activation require at least one hour to manifest (Wehling, M, *Trends Endocrinol Metab.* 56:347–353, 1994), the data demonstrate that a twelve hour pretreatment with RU-486 was not necessary for an RU-486-mediated increase in $APP_S$ secretion. The data also demonstrated that $APP_S$ secretion was not dependent upon a change in gene transcription.

FIG. 5 depicts a western blot which shows varying intensities in $APP_S$ isoforms, most likely due to variations in post-translational processing of isoforms. Since each band shows corresponding changes upon treatment with RU-486, it can be concluded that RU-486 affects the release of all isoforms of $APP_S$, although subtle isoform selective effects have not been ruled out. The increase in $APP_S$ secretion with PMA confirms published findings (Buxbaum, J. D. et al., "Processing of Alzheimer β/A4 amyloid precursor protein: Modulation by agents that regulate protein phosphorylation", Proc. Natl. Acad. Sci. USA 87:6003–6006 (1990); Caporaso, G. L. et al., "Protein phosphorylation regulates secretion of Alzheimer β/A4 amyloid precursor protein", Proc. Natl. Acad. Sci. USA 89:3055–3059 (1992); Mills, J. and P. B. Reiner, "Phorbol esters but not the cholinergic agonists oxotremorine-M and carbachol increase release of the amyloid precursor protein in cultured rat cortical neurons", J Neurochem. 67:1511–1518 (1996)) and give assurance that the cells used in the experiments are biochemically viable.

IV. Determining Whether RU-486 Acts Through Steroid Hormone Receptors to Increase $APP_S$ Secretion E82 mouse L-cells were generously provided by Dr. Mark Danielson (Georgetown University, USA). All materials and methods are as described above.

E82 cells were grown in DMEM with 5% FBS and cultured in 75 cm2 flasks from Falcon.

Concentration of and quantification of $APP_S$ were also performed as described above.

RU-486 increases $APP_S$ release from E82 cells. These cells (Housley, P. R. and Forsthoefel, A. M., Isolation and characterization of a mouse L cell variant deficient in glucocorticoid receptors, Biochem. Biophys. Res. Comm. 164:480–487, 1989)) lack steroid hormone receptors with which RU-486 is known to interact, e.g., the glucocorticoid and progesterone receptors (Baulieu, Science 245:1351–1357, 1989). The increase in $APP_S$ secretion using RU-486 in these cells (FIG. 6) further demonstrates that the observed effects occurs independent of RU-486 activity at steroid hormone receptors.

In western blots probing for $APP_S$ secretion in E82 cells, only two isoform bands of $APP_S$ appeared (FIG. 6) compared to the three bands seen in those using PC12 cells (FIGS. 1, 3, 5). This was attributed to the differences in maturation of $APP_S$ isoforms between cell lines.

V. Demonstration That Three Different P-glycoprotein Blockers Increase $APP_S$ Secretion in Wild Type PC12 Cells Materials and methods utilized were as outlined above. Dexamethasone was purchased from Sigma. Progesterone (HBC complex) and desmethoxyverapamil were purchased from Research Biochemicals Inc.

Treatment groups were as follows: a) Control; b) PMA (0.1 μM); c) RU-486 (0.1 μM); d) dexamethasone (0.1 μM); progesterone (1 μM); desmethoxyverapamil (1 μM).

Figure 8:
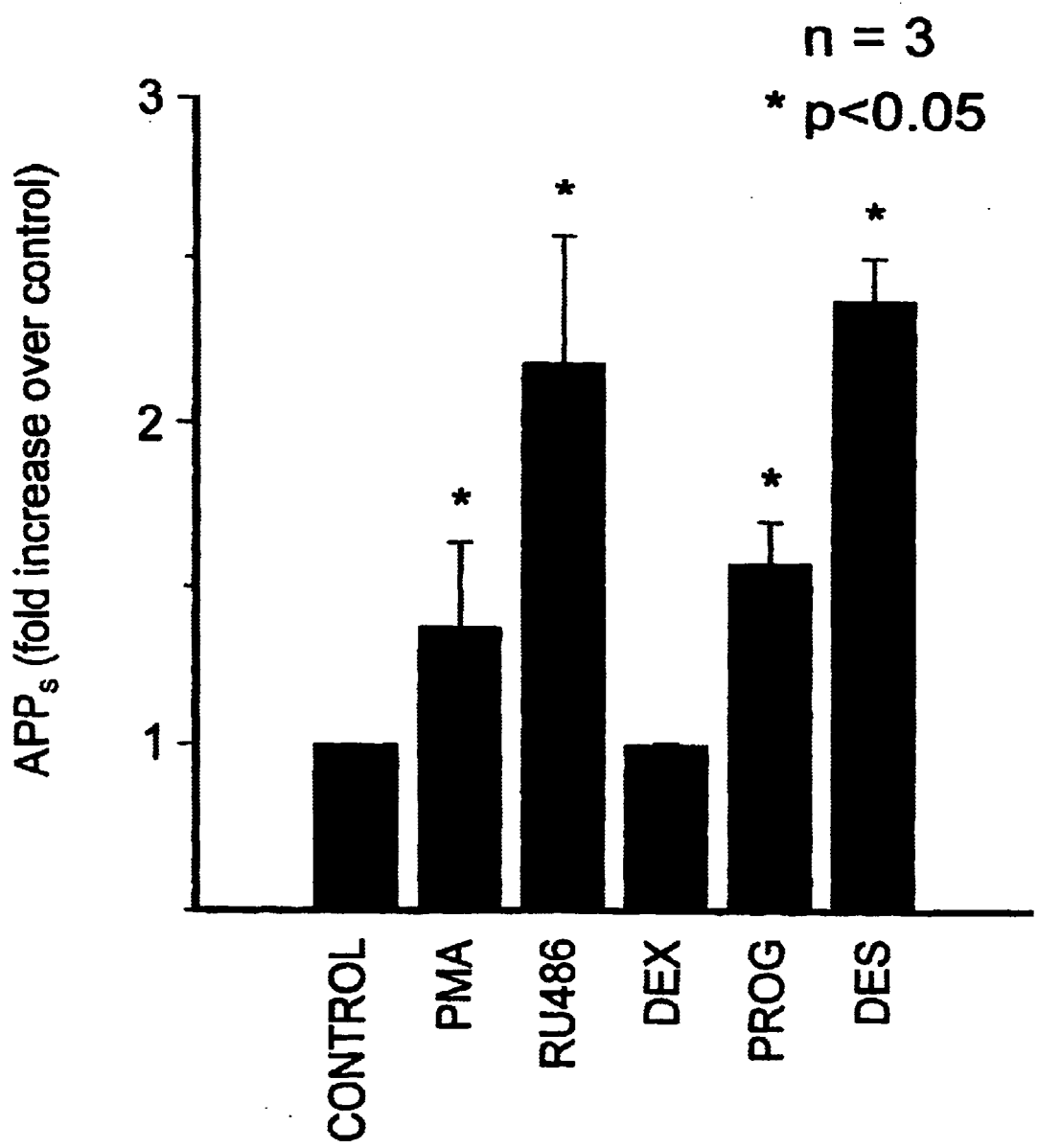
FIG. 8 is a graph of relative increase of $APP_S$ in FIG. 7.

Fifteen minute exposure of PC12 cells to RU-486, progesterone and desmethoxyverapamil significantly increased $APP_S$ secretion from PC12 cells. (FIG. 7 and FIG. 8).

Therefore, it was determined that these therapeutic drugs act as p-glycoprotein blockers. As a negative control, the steroid hormone receptor agonist dexamethasone, which is transported by p-glycoprotein but is not known as a p-glycoprotein blocker was included; it did not significantly increase $APP_S$ secretion. These data represent pharmacological evidence that blockade of p-glycoprotein alters APP catabolism.

VI. Effect of RU-486 on a Human Carcinoma Cell Line; No Increased Production of $APP_S$ A KB-3.1 human carcinoma cell line, expressing low levels of the human MDR1 gene encoding P-glycoprotein gene product (Shen et al., 1986, Science, 232; 643-5), was obtained as a gift from Dr. Ira Pastan (National Cancer Institute, USA). These cells were grown in DMEM with 10% FBS. All materials and methods are as outlined as above.

KB-3.1 cells expressing sub-detectable levels of p-glycoprotein lack modulation of $APP_S$ by RU-486 (FIG. 9). This experiment directly addresses the involvement of p-glycoprotein in regulating APP catabolism. The observation that cells having low expression of p-glycoprotein do not regulate $APP_S$ secretion either by RU-486 or PMA (FIG. 9) suggests that the catabolism of APP may be linked in some fashion to the level of expression of p-glycoprotein. Western blots were performed on PC12, E82, and KB-3.1 cells probing for cellular levels of p-glycoprotein. Detectable levels of the protein were found in PC12 and E82 cells, but none in KB-3.1 cells (data not shown). Although this experiment is not conclusive nor definitive in implicating p-glycoprotein as the only molecule underlying RU-486 mediated $APP_S$ increase, it does provide direct support for this belief.

VII. Transfection of pHaMDR1 Construct Into KB-3.1 Cells Induces $APP_S$ Release KB-3.1 cells were grown as described above. The pHaMDR1 plasmid construct encoding human MDR1 was obtained as a gift from Dr. Ira Pastan (National Cancer Institute).

For calcium-phosphate transfections, cells were plated onto 10 cm polypropylene petri dishes (Falcon) at a density of 2.0×10⁶ cells/dish. To prepare the cDNA for transfection, 15 μg/plate of pHaMDR1 cDNA was mixed together with 1/10 volumes of 3M sodium Acetate, ~3× volume of 100% ethanol in a 1.5 ml eppendorf tube and spun in a desktop centrifuge for thirty seconds. The tube was then filled to the top with ethanol and spun at 15,000 rpm at 4° C. for ten minutes. The ethanol was aspirated, leaving a tiny pellet of cDNA on the bottom. In a sterile fumehood, the cDNA was resuspended with 450 μl of 0.1× tris-EDTA(TE) ethylene diamine tetraacetic acid, tris EDTA and 50 μl of 2.5 M $CaCl_2$. 500 μL of 2× BES (50 mM N,N-bis[2-Hydroxyethyl]-2-aminoethanesulfonic acid, 280 mM NaCl, 1.5 mM $Na_2HPO4.2H_2O$, pH 6.96) was added to make a final volume of 1.0 ml. The entire mixture was allowed to sit for twenty minutes before adding the contents to the plate of cells. Plates were placed in a 3% $CO_2$ incubator for 8–10 hours. The transfection was stopped by aspirating the media, washing the cells twice with ~5 of media and replating the cells onto poly-D-lysine (SIGMA)-coated 10 cm petri dishes at a density of 2.0×10⁶ cells/dish. Cells were left to adhere and then the medium was replaced with DMEM supplemented with 10% charcoal-stripped calf serum prepared twelve hours prior to the drug exposure. To assay for transfection efficiency, the β-galactosidase (β-gal) gene was also co-transfected into the cells. β-gal staining was performed to determine the percentage of cells within each dish which were successfully transfected with the cDNA.

Exposures were performed without resuspending the cells, in contrast to previous experiments described above. 10 ml solutions of DMEM containing either control (DMSO), PMA(0.1 μM) or RU-486 (0.1 μM) were prepared. DMSO concentrations in the medium were normalized to 0.01%(v/v). The supplemented medium was aspirated and 1 ml of the appropriate medium was added to the cells. Dishes were returned to the incubator for fifteen minutes and the medium harvested and processed as previously described. The plated cells were lysed using 100 μl of met/lysis buffer and harvested with cell scrapers (Falcon). 5 μl from each sample was collected for protein quantification. Protein determination and $APP_S$ quantification were performed as previously described.

Figure 10:
FIG. 10 is a western blot of an SDS-PAGE gel demonstrating that transfection of KB-3.1 cells with an expression vector for the human p-glycoprotein gene restores regulation of $APP_S$ release by RU-486.

Transient transfection of the human MDR1 gene into the KB-3 cell line restored regulation of $APP_S$ secretion by PMA and RU-486 (FIG. 10). This experiment suggests that the presence of the MDR1 gene protein product known as p-glycoprotein confers modulation of $APP_S$ secretion upon cells. Other members of the ABC superfamily of transporters can serve a similar function, in a fashion analogous to the ability of human p-glycoprotein to replace the function of yeast ABC transporter STE-6 in exporting the mating pheromone a-factor (Raymond, M. et al., "Functional Complementation of Yeast ste-6 by a mammalian Multidrug resistance mdr gene," Science 256:232 (1992)). That a subdetectable endogenous amount of p-glycoprotein is not sufficient to allow regulated $APP_S$ secretion indicates that there must be a threshold titre of p-glycoprotein which must be present in any cell in order for this modulation to occur. β-gal staining of the transfected cells showed a relatively low percent-transfection efficiency (~10–20%), thus, it was assumed that only 10–20% of the cells per dish had been transfected with MDR1. That an overall restoration in the regulation of $APP_S$ secretion by PMA and RU-486 (FIG. 10) could be seen with such a low transfection efficiency indicated that the effect of P-glycoprotein is potent in affecting this modulated secretion.

Protein bands migrated as only one strong band in the Western blot (FIG. 10). This was evident in experiments in which cells were exposed to drugs while plated, compared to when they were in cell suspension (as previously performed). To control against any anomalous effects which could have been due to this modified protocol, the same drug experiments were performed in non-transfected KB-3.1 cells. It was found that there was no regulation of $APP_S$ secretion by RU-486 or PMA, further demonstrating that plated versus suspended cells did not alter the principal findings of enhanced $APP_S$ secretion by RU-486 and PMA.

VIII. RU486 Reduces Aβ Secretion in SW Cells

Figure 11:
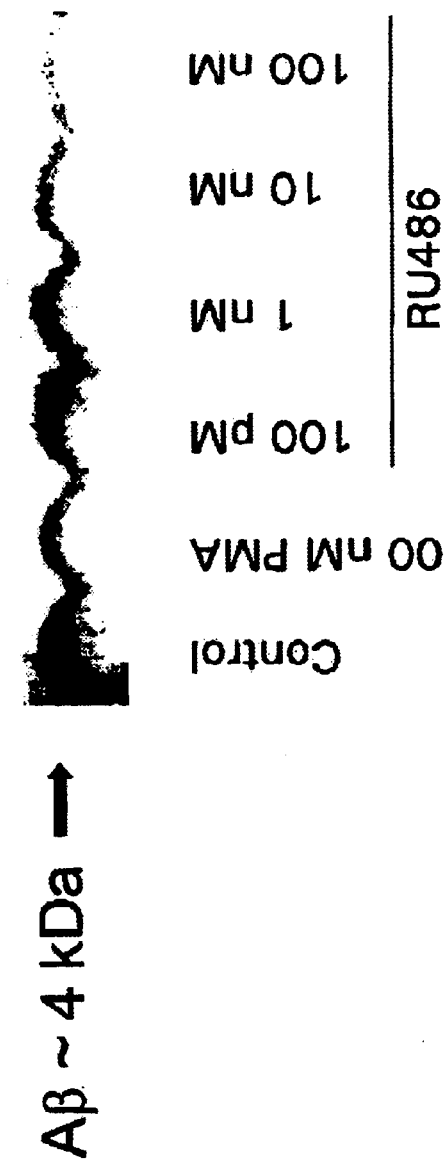
FIG. 11 is a western blot of a SDS-PAGE gel demonstrating that RU-486 decreases the release of $A\beta$ from SW cells.

FIG. 11 demonstrates that RU486, a P-gp blocker reduces Aβ secretion in fifteen minutes in a dose-dependent manner in K269sw cells transiently transfected with the human pHaMDR1 construct. K269sw cells were cultured in 20 mm Falcon dishes in DMEM containing 10% FBS, and 200 mg/mL geneticin (GIBCO) to about 50% confluence and transiently transfected with the human pHaMDR1 construct using the calcium-phosphate precipitation technique as described above. Cells were replated at a density of $2.0 \times 10^6$ cells/dish 8 hours post-transfection on 10 cm petri dishes as described above. To assay for transfection efficiency, the β-gal gene was also co-transfected into the cells. β-gal staining was performed to determine the percentage of cells within each dish which were successfully transfected with the cDNA.

Exposures were performed without resuspending the cells. 10 mL of DMEM containing either control (DMSO), PMA (0.1 μM), or RU486 (0.001 μM, 0.01 μM, 0.1 μM, 1.0 μM), were prepared. DMSO concentrations in the medium were normalized to 0.01% (v/v). The supplemented medium was aspirated and 1 mL of the appropriate medium was added to the cells. Dishes were returned to the incubator for fifteen minutes and the medium harvested and processed as previously described. The plated cells were lysed using 100 μL of met/lysis buffer and harvested with cell scrapers (Falcon). 5 μL from each sample was collected for protein quantification.

Total protein in the harvested media was precipitated using a trichloroacetic acid (TCA) precipitation. TCA corresponding to 1/10 volume of total media was added to each of the 1.5 mL Eppendorf tubes containing harvested media and incubated at ~20° C. for 15 minutes. Protein was immediately pelleted in the tubes with a 14,000 rpm spin at 4° C. for 4 minutes. The supernatant was aspirated, leaving the pellet of precipitated protein. The pellet was washed once with 10% TCA and resuspended in 20 μL of Laemmli buffer.

SDS-PAGE was used to resolve secreted protein on a 16.5% tris-tricine polyacrylamide gel. Protein bands were then transferred onto nitrocellulose membranes (Biorad). Western blotting was then performed using the WO-2 rat monoclonal antibody specific for human Aβ (gift from Konrad Beyreuther). Aβ was visualized using ECL and quantitation was performed as previously described.

IX. RU49953 Reduces Aβ Secretion in SW Cells

FIG. 12 demonstrates that RU49953, a selective P-gp blocker, reduces Aβ secretion in fifteen minutes in a dose-dependent manner in K269sw cells transiently transfected with the human pHaMDR1 construct. Culturing and transient transfection of K269sw cells are as previously described. Preparation of cells for the drug assays are also performed as previously described.

Exposures were performed without resuspending the cells. 10 mL of DMEM containing either control (DMSO), PMA (0.1 μM), or RU49953 (0.01 μM, 0.1 μM, 1.0 μM), were prepared. DMSO concentrations in the medium were normalized to 0.01% (v/v). The supplemented medium was aspirated and 1 mL of the appropriate medium was added to the cells. Dishes were returned to the incubator for fifteen minutes and the medium harvested and processed as previously described. The plated cells were lysed using 100 μL of met/lysis buffer and harvested with cell scrapers (Falcon). 5 μL from each sample was collected for protein quantification.

Total protein in the harvested media was precipitated using a trichloroacetic acid (TCA) precipitation. TCA corresponding to 1/10 volume of total media was added to each of the 1.5 mL Eppendorf tubes containing harvested media and incubated at ~20° C. for 15 minutes. Protein was immediately pelleted in the tubes with a 14,000 rpm spin at 4° C. for 4 minutes. The supernatant was aspirated, leaving the pellet of precipitated protein. The pellet was washed once with 10% TCA and resuspended in 10 μL of Laemmli buffer.

SDS-PAGE was used to resolve secreted protein on a 16.5% tris-tricine polyacrylamide gel. Protein bands were then transferred onto nitrocellulose membranes (Biorad). Western blotting was then performed using the WO-2 rat monoclonal antibody specific for human Aβ (gift from Konrad Beyreuther). Aβ was visualized using ECL and quantitation was performed as previously described.

Figure 14:
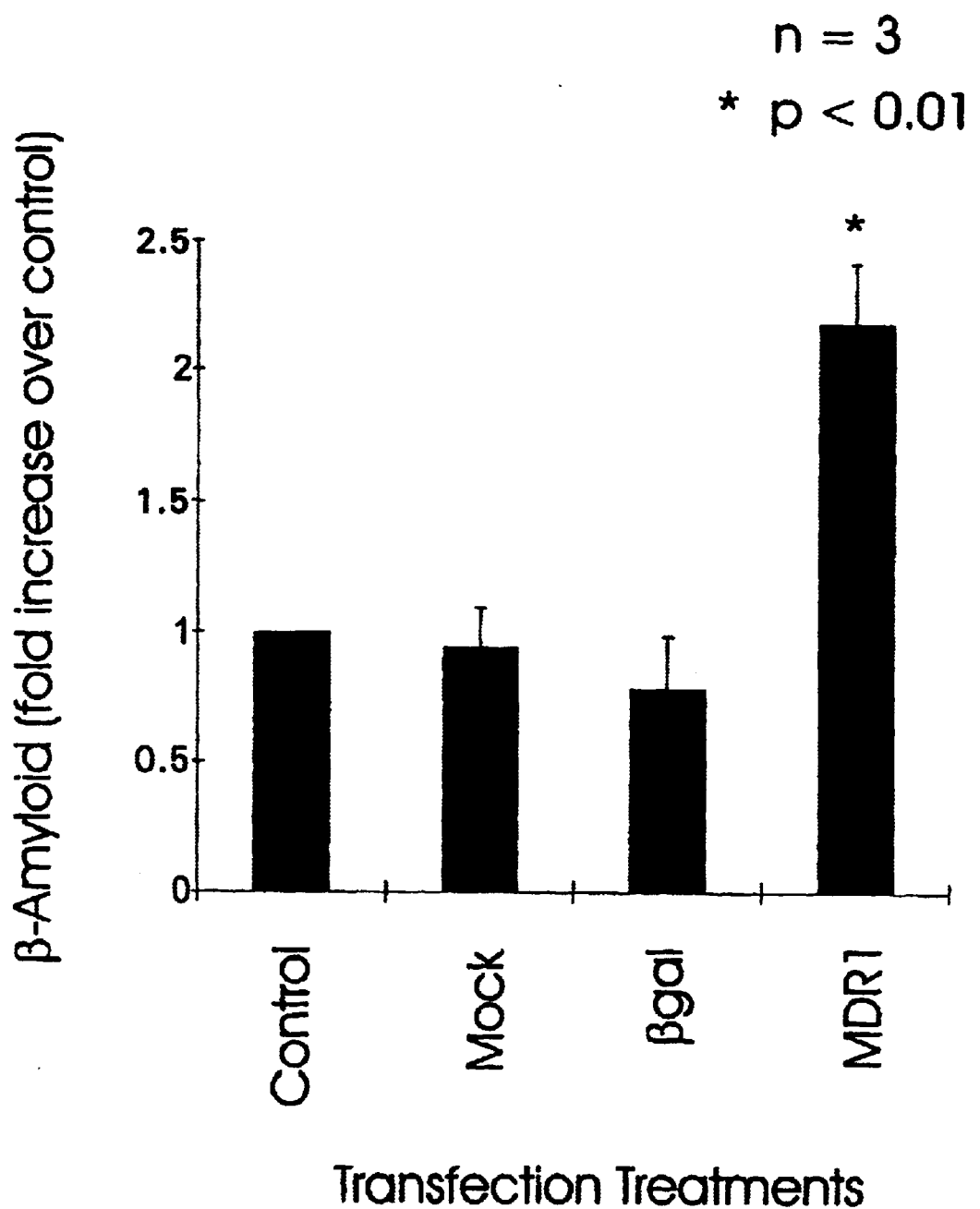
FIG. 14 is a graphic depiction of densitometric analysis of transfected K269sw cells.

X. Transient Transfection of Human MDR1 in K269sw Cells Increases Basal Secretion of β-Amyloid FIGS. 13 and 14 demonstrates that transient transfection of P-glycoprotein in K269sw cells increases basal secretion of β-amyloid. K269sw cells were grown as previously described. Protocols for transient transfection are also as described albeit the following modifications. Individual 20 mm plates of K269sw cells were transfected with the following: control (no calcium-phosphate precipitation); mock (calcium-phosphate precipitation without any plasmid); β-gal (transfection with the β-galactosidase gene); and MDR1 (transfection with the human MDR1 gene). Replating of cells post-transfection was performed as described above.

Basal levels of Aβ secretion were assayed in the following way. Supplemented medium was replaced with 1 mL DMEM and dishes were returned to the incubator for one hour. Conditioned medium was harvested and secreted Aβ was detected and quantified as previously described.

XI. Exemplary in Vitro Screening Assay for Identifying Agents Which Modulate Transport of Aβ Across Membranes An exemplary in vitro screening assay for identifying agents which modulate transport of Aβ across membranes by measuring Aβ transport across the membrane is set forth below.

As a type I transmembrane protein[3], the presumed topography of APP in the bilayer is such that much of the N-terminus is extracellular, making it reasonable that α-secretase cleavage of APP yields $APP_S$ fragments which are simply released into the extracellular milieu. This is not the case for Aβ peptide is likely to be at least partially embedded within the membrane[16]. As such, simple diffusion is an inadequate mechanism to account for Aβ release. We propose a model whereby efflux of membrane-bound Aβ requires active transport via p-gp or another ABC transporter.

Figure 15A:
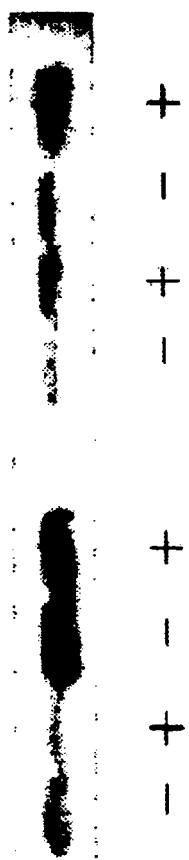
FIG. 15 illustrates results obtained from an exemplary in vitro screening assay for identifying agents which modulate transport of $A\beta$ across membranes by measuring $A\beta$ transport across the membrane, as set forth in further detail in XI of the Exemplification, below.
Figure 15B:
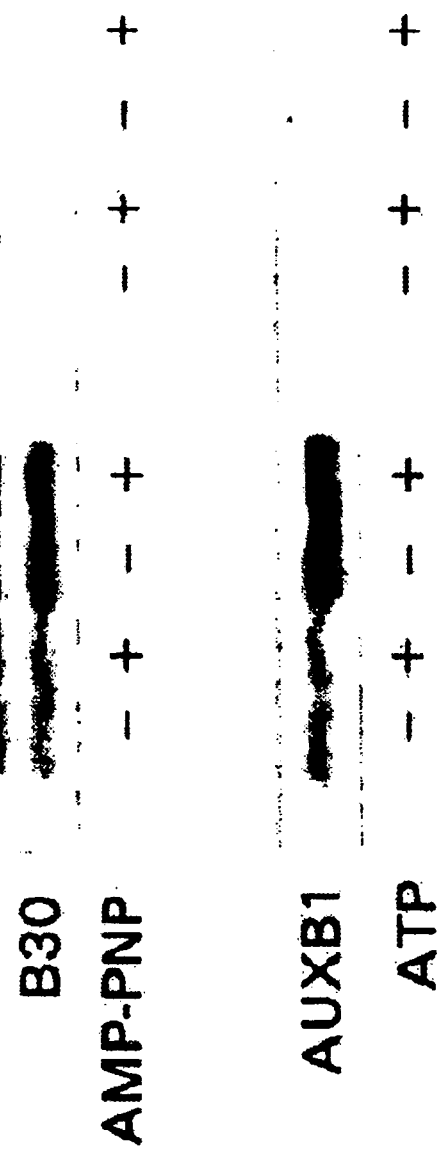
Figure 15C:
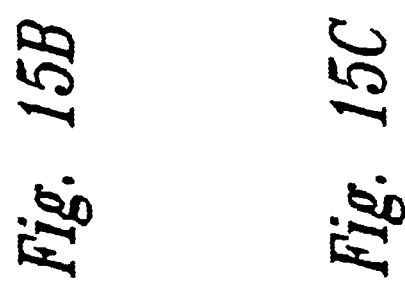
Figure 15D:
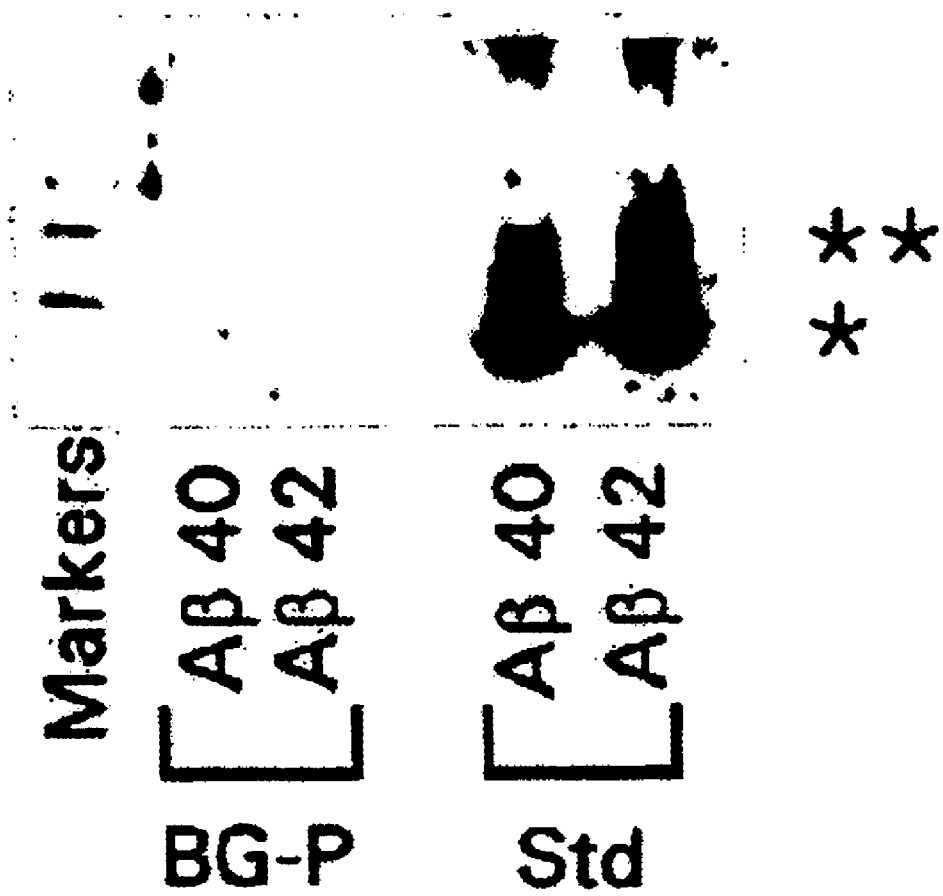
Figure 15E:
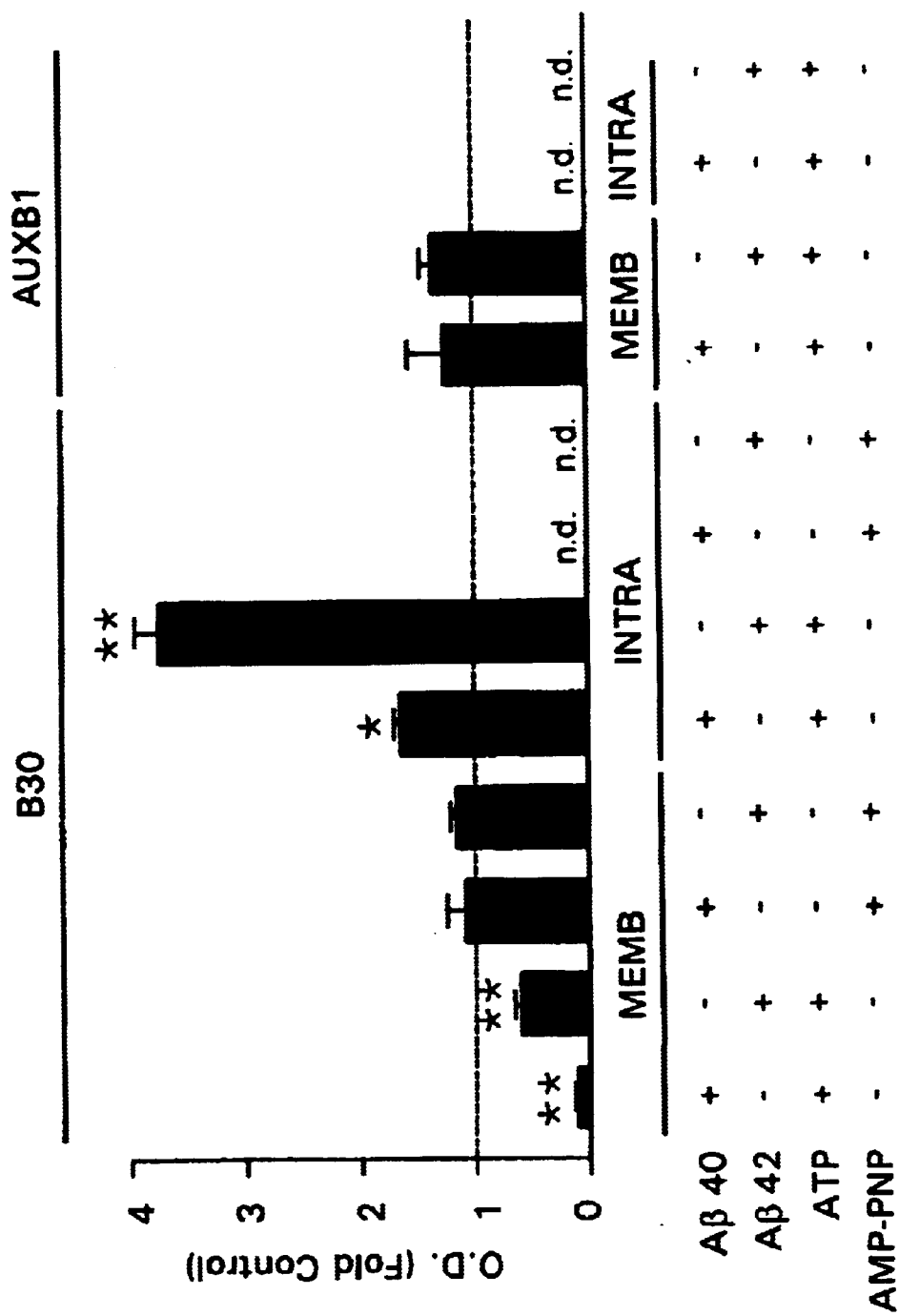

To test this model, we used a reconstituted liposome system derived from multidrug resistance Chinese hamster ovary $CH^R$ B30 cells (B30) enriched in purified hamster class 1 p-gp in an inside-out orientation with the ATP binding-sites situated on the extra-liposomal surface[17]. To mimic the scenario whereby Aβ is partitioned in the membrane, we pre-incubated the liposomes with Aβ to allow for membrane association before activating p-gp by addition of ATP. Excess unbound Aβ was removed by passing the vesicles through a size exclusion column which completely excludes Aβ (FIG. 15D). Levels of Aβ in the membrane and intraliposomal fractions were used as measures of Aβ transport. As predicted by our model, addition of ATP to p-gp enriched vesicles resulted in significant decreases in membrane-associated Aβ and corresponding increases in intraliposomal Aβ (FIG. 15A.) Such changes in Aβ levels in the respective fractions were not observed when ATP was replaced with a non-hydrolysable analogue, AMP-PNP (FIG. 15B). As a further control, we repeated the experiment using liposomes derived from p-gp-deficient chinese hamster ovary AuxB1 cells (the cell line from which the $CH^R$B30 cells had been selected)[18]. There were no significant changes in membrane-associated Aβ upon addition of ATP, and intraliposomal Aβ was not detected under unstimulated conditions nor following addition of ATP in the AuxB1 liposomes (FIG. 15C). These data suggest that p-gp is an Aβ efflux pump.

These findings represent the first experimental evidence for a mechanism of Aβ release from cells. The hypothesis that p-gp acts as an Aβ efflux pump is consistent with the known biology of this transporter: p-gp has a variety of structurally unrelated substrates which have the unifying characteristic of being lipophilic[12], and Aβ is a lipophilic peptide.

Methods: Liposome transport of Aβ. Liposomes derived from AuxB1 (p-gp deficient) and $CH^R$B30 (p-gp enriched) cell lines were incubated at 37° C. for 15 minutes with 100 nM Aβ1-40/1-452 (US Peptides Inc.) to allow for peptide association with the membrane. Excess Aβ was removed by passing the liposomes through a BioGel P-6 size exclusion column (BioRad). A final concentration of 1.5 mM $Na_4ATP$ (Sigma) or AMP-PNP (Sigma) was added to the liposomes to activate p-gp and the entire preparation was left to react for 15 minutes at 37° C. Samples were then subjected to 5 cycles of rapid freeze-thaw in liquid nitrogen to lyse the liposomes, then centrifuged at 100,000 g for 20 minutes to pellet the membranes. A TCA precipitation was performed on the supernatant fraction containing intraliposomal Aβ peptide followed by resuspension in Laemmli buffer, while the pellet fraction (containing membrane-bound Aβ) was directly resuspended in Laemmli buffer. Both fractions were resolved using SDS-PAGE and western blotting was used to detect Aβ.

FIG. 15 illustrates P-gp mediated transport of Aβ peptides in an ATP-dependent manner. FIG. 15A shows B30 liposomes enriched in hamster class 1 p-gp transports pre-inserted synthetic human Aβ1-40 and 1-42 peptides in an ATP-dependent manner (n=3). In this and subsequent panels, western blots using the 6E10 antibody show levels of membrane-bound Aβ peptides ($Aβ_{MEMB}$) and their corresponding levels in the interior of the liposome ($Aβ_{INTRA}$) before and after addition of nucleotide. FIG. 15B shows that the non-hydrolysable analogue of ATP, AMP-PNP, does not stimulate transport of Aβ into B30 liposomes (n=2). FIG. 15C illustrates that ATP-dependent transport is also absent in p-gp deficient AuxB1 liposomes (n=3). No Aβ was detectable in the interior of liposomes of B30 and AuxB1 vesicles treated with AMP-PNP or ATP, respectively, using western blotting. FIG. 15D shows overexposed a western blot of synthetic Aβ peptides spun through a Biogel-P6 size exclusion column (BG-P) compared to standards (Std). 100 nM Aβ standards develop an intense signal while eluant collected from solution containing 100 nM Aβ spun through BioGel-P6 columns show no detectable signal even after overexposure of the blot to ECL film. Molecular weight markers are shown on the left of the figure (Markers). The single asterisk indicates monomeric Aβ at 4 kDa; double asterisks indicates Aβ dimers at 8 kDa. Aβ was detected using the WO-2 monoclonal antibody. e, Quantification of direct transport assay results. Average O.D. values are normalized to their respective controls (no ATP or AMP-PNP treatment; dashed line; * $p<0.05$ and ** $p<0.01$). MEMB represents membrane-bound Aβ, INTRA represents Aβ in the liposomse interior, and n.d. represents non-detectable Aβ signal. Results are average O.D.±s.e.m. of individual experiments repeated in times.

REFERENCES

1. Hardy, J. The Alzheimer family of diseases: many etiologies, one pathogenesis? *Proc. Natl. Acad. Sci. USA* 94, 2095–2097 (1997).
2. Duff, K. Alzheimer transgenic mouse models come of age. *Trends Neurosci* 20, 279–280 (1997).
3. Selkoe, D. Amyloid β-protein and the genetics of Alzheimer's disease. *J Biol. Chem.* 271, 18295–18298 (1996).
4. Higgins, C. F. The ABC of channel regulation. *Cell* 82, 693–696 (1995).
5. Mills, J. and Reiner, P. B. Regulation of amyloid precursor protein cleavage. *J Neurochem*, in press.
6. Kremer, N. E. et al. Signal transduction by nerve growth fractor and fibroblastgrowth factor in PC12 cells requires a sequence of Scr and Ras actions. *J Cell Biol* 115, 809–819 (1991).
7. Tsai, M-J. and O'Malley, B. W. Molecular mechanisms of action of steroid/thyroid receptor superfamily members. *Annu Rev Biochem.* 63, 451–486 (1994).
8. Allan, G. F. et al Hormone and antihormone induce distinct conformational changes which are central to steroid receptor activation. *J Biol. Chem* 267m 19513–19520 (1992).
9. LeBeau, M-C. and Baulieu, E. F. Steroid antagonists and receptor-associated proteins. *Human Reproduction* 9 Suppl. 2, 11–21 (1994).
10. Housely, P. R. and Forsthoefel, A. M. Isolation and characterization of a mouse L cell variant deficient in glucocorticoid receptors. *Bioch Biophys Res Comm* 164, 480–487 (1989).
11. Gruol, D. J. et al Reversal of multidrug resistance by RU486. *Cancer Res.* 54, 3088–3091 (1994).
12. Ford, J. M. and Hait, W. N. Pharmacology of drugs that alter multidrug resistance in cancer. *Pharm. Rev.* 42, 155–199 (1990).
13. Ueda, K. et al. The human multidrug resistance (MDR1) gene. cDNA cloning and transcription initiation. *J Biol. Chem.* 262, 505–508 (1987).
14. Citron, M. et al. Evidence that the 42- and 40-amino acid forms of amyloid β protein are generated from the β-amyloid precursor protein by different protease activities. *Proc. Natl. Acad. Sci. USA* 93, 13170–13175 (1996).
15. Marsaud, V. et al. Dexamethasone and triamcinolone acetonide accumulation in mouse fibroblasts is differently modulated by the immunosuppressants cyclosporin A, FK506, rapamycin and their analogues, as well as by other P-glycoprotein ligands. *J Steroid Bioch. Mol. Biol.* 66, 11–25 (1998).
16. Tischer, E. and Cordell, B. β-amyloid precursor protein. Location of transmembrane domain and specificity of γ-secretase cleavage. *J Biol. Chem.* 271, 21914–21919 (1996).
17. Shapiro, A. B. & Ling, V. Reconstitution of drug transport by purified p-glycoprotein. *J Biol. Chem.* 270, 16167–16175 (1995).
18. Kartner, N., Evernden-Porelle, D., Bradley, G., and Ling, V. Detection of p-glycoprotein in multidrug-resistance cell lines by monoclonal antibodies. *Nature* 316, 820–823 (1985).
19. Simons, M. et al. Amyloidogenic processing of the human amyloid precursor protein in primary cultures of rat hippocampal neurons. *J Neurosci.* 16, 899–908 (1996).
20. Demeule, M. et al. Molecular interactions of cyclosporin A with p-glycoprotein. Photolabelling with cyclosporin derivatives. *J Biol. Chem.* 272, 6647–6652 (1997).
21. Snyder, S. H., Lai, M. M., and Burnett, P. E. Immunophilins in the nervous system. *Neuron* 21, 283–294 (1998).
22. Mattson, M. P. Cellular actions of beta-amyloid precursor protein and its soluble and fibrillogenic derivatives. *Physiol Rev.* 77, 373–375 (1997).
23. Thiebaut, F. et al. Cellular localization of the multidrug-resistance gene product p-glycoprotein in normal human tissues. *Proc. Natl. Acad. Sci. USA* 84, 7735–7738 (1987).
24. Regina, A., et al. Mrp1 multidrug resistance-associated protein and p-glycoprotein expression in rat brain microvessel endothelial cells. *J Neurochem.* 71, 705–715 (1998).
25. Van Veen, H. W. et al. A bacterial antibiotic-resistance gene that complements the human multidrug-resistance P-glycoprotein gene. *Nature* 391, 291–295 (1998).
26. Raymond, M., Gros, P., Whiteway, M., and Thomas, D. Y. Functional complementation of yeast ste6 by a mammalian multidrug resistance mdr gene. *Science* 256, 232–234 (1992).
27. Ruetz, S. et al. Functional expression of the multidrug resistance-associated protein in the yeast *Saccharomyes cerevisiae*. 271, 4154–4160 (1996).
28. Mills, J. et al. Regulation of amyloid precursor protein catabolism involves themitogen-activated protein kinase signal transduction pathway. *J Neurosci.* 17, 9415–422 (1998).
29. Raymond, L. M., Moshaver, A., Tingle, W. G., Shalaby, I., and Huganir, R. L. Glutamate receptor ion channel properties predict vulnerability to cytotoxicity in a transfected non-neuronal cell line. *Mol. Cell. Neurosci.* 7, 102–115 (1996).
30. Weidmann, A. et al. Identification, biogenesis, and localization of precursors of Alzheimer's disease A4 amyloid protein. *Cell* 57, 115–126 (1989).
31. Ida, N. et al. Analysis of heterogeneous βA4 Peptides in human cerebrospinal fluid and blood by a newly developed sensitive western blot assay. *J Biol. Chem.* 271, 22908–22914 (1996).

Equivalents

Those skilled in the art will know, or be able to ascertain, using no more than routine experimentation, many equivalents to the specific embodiments of the invention described herein. These and all other equivalents are intended to be encompassed by the following claims.

What is claimed is:

1. A method of inhibiting the export of amyloid-β (Aβ) from a cell, comprising administering to a subject an effective amount of transporter blocker for an ATP binding cassette (ABC) transporter, wherein the transporter blocker is RU-49953, and wherein said transporter is responsible for export of Aβ from said cell, such that export of Aβ is inhibited.

2. The method of claim 1, wherein said administration of said ABC transporter blocker prevents or inhibits amyloid deposition.

3. The method of claim 1, wherein said ABC transporter blocker is a blocker of the ABC transporter MDR1, MDR3, ABC1, ABC2, ABC3, ABC7, ABC8, MRP4, or MRP5.

* * * * *

UNITED STATES PATENT AND TRADEMARK OFFICE
CERTIFICATE OF CORRECTION

PATENT NO.      : 6,660,725 B1
APPLICATION NO. : 09/643511
DATED           : December 9, 2003
INVENTOR(S)     : Peter B. Reiner et al.

It is certified that error appears in the above-identified patent and that said Letters Patent is hereby corrected as shown below:

Column 36, line 51, "amount of transporter blocker" should read --amount of a transporter blocker--.

Column 36, line 57, "transporter blocker prevents or inhibits" should read --transporter blocker inhibits--.

Column 14, line 46, "cylcosporine" should read --cyclosporine--.

Column 14, lines 50-52, "(17β-hydroxy-11β, 17α-[4-dimethylaminophenyl] - 17α prop-1-ynyl estra-4, 9 dien-3 one)" should read --(11β, 17α di[4-(dimethylamino)phenyl [estra-1,3,5(10)-triene-3, 17β-diol)--.

Column 16, lines 22-24, "(17b-hydroxy-11b, 17a-[4-dimethylaminophenyl]- 17a prop-1-ynyl estra-4, 9-dien-3 one)" should read --(11β, 17α di[4-(dimethylamino)phenyl[estra-1,3,5(10)-triene-3, 17β-diol)--.

Signed and Sealed this

Twenty-ninth Day of August, 2006

JON W. DUDAS
*Director of the United States Patent and Trademark Office*